(12) United States Patent
Choi et al.

(10) Patent No.: US 11,151,802 B2
(45) Date of Patent: Oct. 19, 2021

(54) METHOD AND SYSTEM FOR PROVIDING A FACE ADJUSTMENT IMAGE

(75) Inventors: Heung-san Choi, Seoul (KR); Jin-su Kim, Seoul (KR); Young-guk Park, Seoul (KR); Seung-hak Baek, Seoul (KR); Sang-hwan Joo, Seoul (KR); Hyung-jun Cho, Seoul (KR)

(73) Assignee: MORPHEUS CO., LTD., Seoul (KR)

( * ) Notice: Subject to any disclaimer, the term of this patent is extended or adjusted under 35 U.S.C. 154(b) by 0 days.

(21) Appl. No.: 14/001,037

(22) PCT Filed: Feb. 9, 2012

(86) PCT No.: PCT/KR2012/000975
§ 371 (c)(1),
(2), (4) Date: Aug. 22, 2013

(87) PCT Pub. No.: WO2012/115373
PCT Pub. Date: Aug. 30, 2012

(65) Prior Publication Data
US 2013/0328869 A1    Dec. 12, 2013

(30) Foreign Application Priority Data
Feb. 22, 2011 (KR) .......... 10-2011-0015529

(51) Int. Cl.
G06T 19/20 (2011.01)
G06T 7/33 (2017.01)
G16H 50/50 (2018.01)

(52) U.S. Cl.
CPC .......... *G06T 19/20* (2013.01); *G06T 7/33* (2017.01); *G06T 2207/10028* (2013.01);
(Continued)

(58) Field of Classification Search
CPC .................................................. G06T 19/20
(Continued)

(56) References Cited

U.S. PATENT DOCUMENTS

2002/0035458 A1* 3/2002 Kim .......... G06T 15/00
703/6
2002/0176612 A1* 11/2002 Tuncay .......... G09B 23/30
382/128
(Continued)

FOREIGN PATENT DOCUMENTS

KR 10-2004-0075672 A 8/2004
KR 10-2009-0115884 A 11/2009

OTHER PUBLICATIONS

International Search Report for PCT Application No. PCT/KR2012/000975, Korean Intellectual Property Office, dated Sep. 26, 2012.
(Continued)

*Primary Examiner* — Shivang I Patel
(74) *Attorney, Agent, or Firm* — Dinsmore & Shohl LLP; Yongsok Choi, Esq.

(57) ABSTRACT

The present invention relates to a method and system for providing a face adjustment image, the method comprising the steps of: (a) generating a matched image by superimposing a cephalometric image having a cranium image of a patient whose face is to be corrected with a three-dimensional facial image of the patient; and (b) displaying a predicted facial image on a screen by transforming soft skin tissues of the face according to the skeletal change in the cephalometric image. According to the present invention, the change in the soft skin tissues and the predicted facial image are displayed on a screen of a computer, a terminal or the like based on the skeletal change in cranium, teeth, prosthesis or the like supporting the soft skin tissues. Therefore, the change in the soft skin tissues can be predicted, thereby increasing the accuracy of a face correction operation, making it more accurate and convenient to plan the operation, and enhancing communication between the patient and medical staff.

20 Claims, 20 Drawing Sheets

(52) U.S. Cl.
CPC ............... *G06T 2207/10116* (2013.01); *G06T 2207/20101* (2013.01); *G06T 2207/30004* (2013.01); *G06T 2207/30201* (2013.01); *G06T 2210/41* (2013.01); *G06T 2219/2021* (2013.01); *G16H 50/50* (2018.01)

(58) Field of Classification Search
USPC ......................................................... 345/419
See application file for complete search history.

(56) References Cited

U.S. PATENT DOCUMENTS

| | | | | |
|---|---|---|---|---|
| 2004/0029068 | A1* | 2/2004 | Sachdeva ................. | A61C 7/00 433/24 |
| 2004/0197727 | A1* | 10/2004 | Sachdeva ................. | A61C 7/00 433/24 |
| 2007/0299551 | A1 | 12/2007 | Weinzweig et al. | |
| 2008/0124064 | A1* | 5/2008 | Klinghult et al. .............. | 396/50 |

OTHER PUBLICATIONS

Written Opinion of the International Searching Authority for PCT Application No. PCT/KR2012/000975, Korean Intellectual Property Office, dated Sep. 26, 2012.

\* cited by examiner

METHOD AND SYSTEM FOR PROVIDING A FACE ADJUSTMENT IMAGE

FIELD OF THE INVENTION

The present invention relates to a method and system for providing a face adjustment image, and more specifically, to a method and system for providing a face adjustment image to display a predicted facial image to confirm an operation plan before performing a face correction operation by using face correction techniques such as surgical plastic surgery or orthodontic therapy.

BACKGROUND

For the modern people, looks, particularly facial looks are one of the criteria to make decisions in job interviews or school admission interviews, and play very important roles in social life such as personal relationship. Therefore, plastic surgery, particularly surgical facial plastic surgery prevails.

Recently, virtual simulation programs to display a predicted facial image resulting from a face correction operation before performing the operation are being developed and provided to the medical staff of clinics such as plastic surgery clinics, so that the medical staff may set up face correction strategy by using the virtual simulation programs during surgery counseling and provide the predicted facial image to confirm an operation plan.

However, the above-mentioned virtual simulation programs display a two-dimensional image by photographing the face of the patient on a monitor screen and modify the two-dimensional image to display the predicted facial image, which is different from the actual appearance after the operation. Moreover, the actual operation involves the correction of osseous tissues, which makes it difficult to set up the plan and method of the operation.

Meanwhile, besides the above-mentioned plastic surgery, other examples of the face correction techniques include orthodontic treatments to improve the malalignment of teeth or orthodontic therapies such as corrective orthognathic surgery in which surgical operations are performed on maxillary bones to improve mandibular prognathism or short chin.

In other words, the above-mentioned orthodontic therapies include the correction of the malalignment such as orthodontic treatments to simply straighten irregular teeth, which contributes to the health of oral tissues, by correcting various skeletal incongruities that may occur during the growth to recover normal functions, and beautifies the facial line to make good-looking facial features.

The above-mentioned orthodontic treatments are techniques to improve the malalignment such as malocclusion by realigning the teeth, while the corrective orthognathic surgery allows skeletal improvements by performing surgical operations on maxillary bones.

As described above, since the facial appearance can be significantly changed by the orthodontic treatments or the corrective orthognathic surgery, there is a need for precise prediction of the facial change in advance of the orthodontic treatments to perform proper operations. However, since it is difficult to display the precise predicted appearance change and the prediction of the facial line change simply depends on the two-dimensional modification based on the experience of the operator, the predicted appearance may differ from the actual appearance after the orthodontic treatment and there is also difficulty in setting up the correction plan and method.

Therefore, the inventors have developed a method and system for providing a face adjustment image in which the facial appearance change can be predicted and displayed with high precision by transforming soft skin tissues of the face according to the change in the skeleton supporting the soft skin tissues.

SUMMARY OF THE INVENTION

One object of the present invention is to provide a method and system for providing a face adjustment image in which the change in facial appearance images can be previewed based on the transformation of soft skin tissues according to the change in the skeleton of the head supporting the soft skin tissues.

Another object of the present invention is to provide a method and system for providing a face adjustment image in which the superimposition of facial appearance images and cranium images can be performed precisely and easily.

According to one aspect of the present invention to achieve the above-mentioned objects, there is provided a method and system for providing a face adjustment image, the method comprising the steps of: (a) generating a matched image by superimposing a cephalometric image having a cranium image of a patient whose face is to be corrected with a three-dimensional facial image of the patient; and (b) displaying a predicted facial image on a screen based on the transformation of soft skin tissues in the matched image. The step (b) is displaying the predicted facial image based on the change in the soft skin tissues according to the skeletal change in the cephalometric image.

In the step (a), a plurality of first alignment points arranged on the facial image to superimpose the facial image and the cephalometric image are matched with a plurality of second alignment points arranged on the positions corresponding to those of the first alignment points on the outline of the cephalometric image, which is formed by the soft skin tissues, so that the facial image and the cephalometric image are superimposed.

The step (a) herein may comprise (a1) receiving inputs for the first alignment points and the second alignment points, and (a2) displaying the facial image being superimposed with the cephalometric image on the screen.

Preferably, the step (a) may further comprise (a3) adjusting the size and orientation of the cephalometric image to the same as those of the facial image.

The first alignment points herein comprise a pair of facial alignment points, and the second alignment points comprise a pair of outline alignment points located on the positions corresponding to those of the facial alignment points. The step (a3) is performed by matching the size and orientation of a first vector formed by the facial alignment points and a second vector formed by the outline alignment points.

In addition, the step (a) may further comprise (a4) displaying matching alignment lines on the screen. The alignment lines are respectively formed on the first alignment points before the step (a1), and their orientations and lengths may be adjusted to achieve one-to-one correspondence of the first alignment points to the second alignment points.

The step (a) generates the matched image by superimposing the cephalometric image on the cross section of the facial image divided by a matching reference line arranged on the facial image.

The matching reference line herein is a vertical line dividing the facial image to the left and right sides, and the cephalometric image may be a lateral image obtained by photographing the head of the patient on the lateral side perpendicular to the front side of the face.

Furthermore, the step (a) may display one lateral side of the facial image divided by the cephalometric image transparently on the screen so that the cephalometric image may be displayed on the screen.

The step (b) may comprise (b1) determining the change in the soft skin tissues corresponding to the skeletal change in the head, and (b2) displaying the predicted facial image on the screen based on the change in the soft skin tissues.

The skeletal change in the head results from at least one of tooth migration and cranial transformation.

The step (b2) selectively displays contour lines for showing the change in the soft skin tissues on the predicted facial image.

The step (b) may display the predicted facial images before and after the simulation on the screen simultaneously or sequentially.

According to another aspect of the present invention, there is provided a system for providing a face adjustment image, comprising: a matching module to generate a matched image by superimposing a cephalometric image having a cranium image of a patient whose face is to be corrected with a three-dimensional facial image of the patient; and an image display module to display a predicted facial image on a screen based on the transformation of soft skin tissues in the matched image.

According to still another aspect of the present invention, there is provided a computer system for providing a face adjustment image, comprising: a first image acquisition unit to acquire a two-dimensional cephalometric image having a cranium image of a patient whose face is to be corrected; a second image acquisition unit to acquire a three-dimensional facial image by photographing the face of the patient; an image storage module to receive and store the cephalometric image and the three-dimensional facial image; a matching module to generate a matched image by superimposing the cephalometric image and the facial image stored in the image storage module; and an image display module to display a predicted facial image on a screen based on the transformation of soft skin tissues in the matched image.

According to yet another aspect of the invention, there is provided a computer-readable recording medium having stored thereon a program for providing a face adjustment image, which enables a computer to function as matching means to generate a matched image by superimposing a cephalometric image having a cranium image of a patient whose face is to be corrected with a three-dimensional facial image of the patient, and image display means to display a predicted facial image on a screen based on the transformation of soft skin tissues in the matched image.

The method and system for providing a face adjustment image according to the present invention bring about the following effects.

First, according to the invention, the change in soft skin tissues and the predicted facial image are displayed on a screen of a computer, a terminal or the like based on the skeletal change in cranium, teeth, prosthesis or the like supporting the soft skin tissues. Therefore, the change in the soft skin tissues can be predicted, thereby increasing the accuracy of a face correction operation, making it more accurate and convenient to plan the operation, and enhancing communication between the patient and medical staff.

Second, according to the invention, the matching of the cephalometric image and the facial image becomes more convenient, and the predicted facial image after the operation may be displayed in three dimensions by utilizing the image matched in precise size and ratio, so that the predicted appearance after the operation becomes more accurate.

Third, according to the invention, both of the images before and after an operation may be displayed on a single screen simultaneously or sequentially to the patient whose face is to be corrected, so that the images before and after the operation may be compared and the operation may be accurately planned.

Fourth, according to the invention, the change in soft tissues and their adjacent parts directly supported by the changing skeleton may be observed in three dimensions, so that the accuracy of the predicted facial image may be improved.

DETAILED DESCRIPTION OF PREFERRED EMBODIMENTS

Hereinafter, the preferred embodiments of the present invention will be described with reference to the accompanying drawings. In describing the embodiments, the same designations and numerals will be used to denote the same elements and additional explanation thereof will be omitted below.

First, one embodiment of a method and system for providing a face adjustment image according to the present invention will be described with reference to FIGS. 1 and 2.

Figure 1:
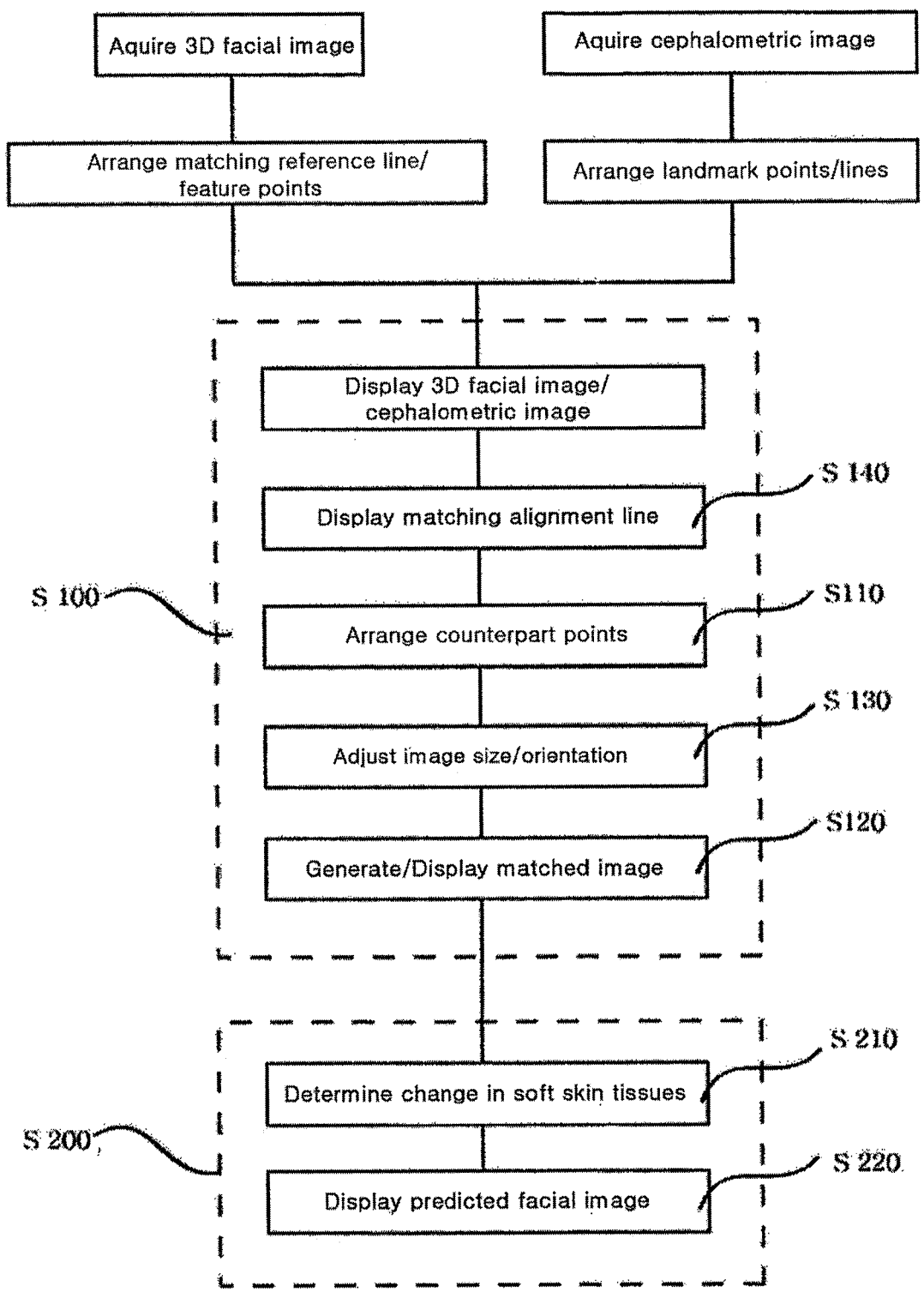
FIG. 1 is a flowchart showing one embodiment of a method for providing a face adjustment image according to the invention.

Referring to FIG. 1, the method for providing a face adjustment image according to the invention comprises the steps of (a) generating a matched image by superimposing a cephalometric image of a patient whose face is to be corrected with a 3D facial image (S120) (i.e., the matched image generation step) and (b) displaying a predicted facial image before a face correction operation (S130) (i.e., the predicted image display step).

Figure 2:
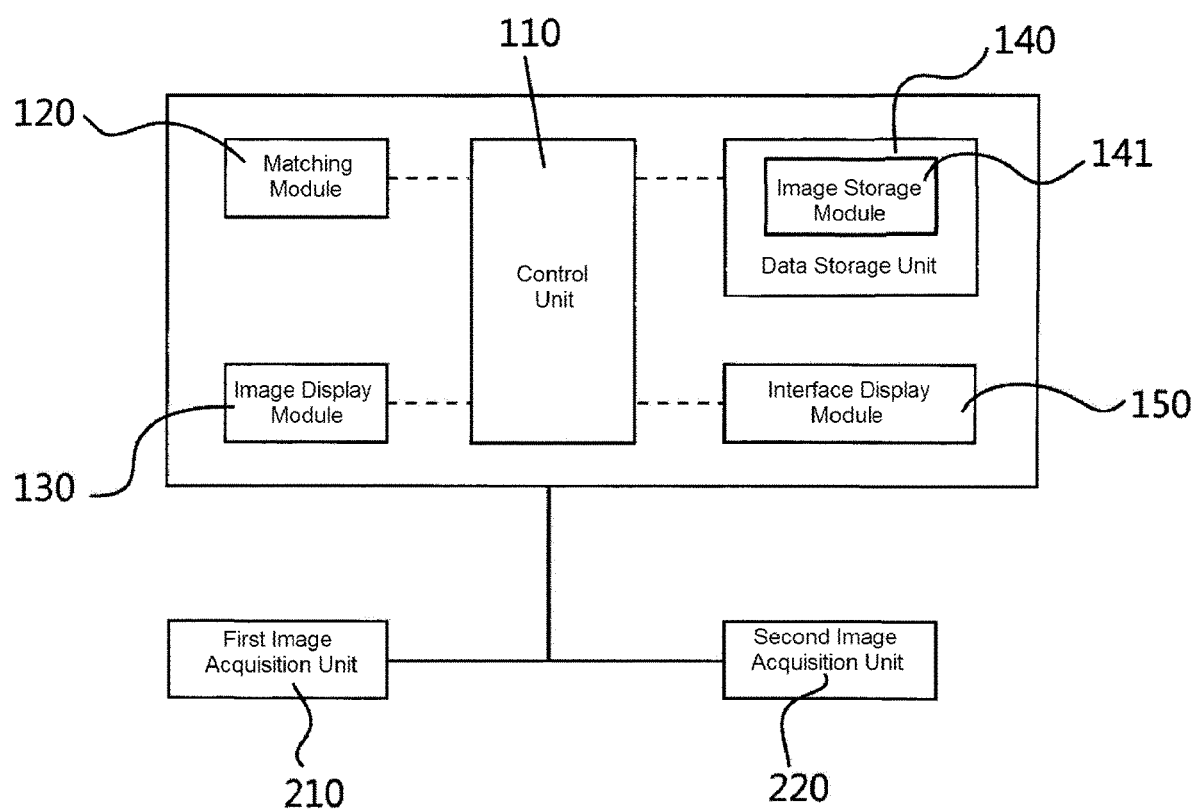
FIG. 2 is a block diagram showing one embodiment of a system for providing a face adjustment image according to the invention.

Next, referring to FIG. 2, the device for providing a face adjustment image according to the invention comprises: a control unit 110 which controls the processing of the face adjustment image; a matching module 120 to generate a matched image by superimposing a cephalometric image of a patient whose face is to be corrected with a 3D facial image; and an image display module 130 to display various images such as predicted images (i.e., predicted facial images) before a face correction operation.

As one example of the above face adjustment image providing device, there may be provided a system for providing a face adjustment image, such as a computer system or a workstation, which comprises a first image acquisition unit 210 to acquire the cephalometric image and a second image acquisition unit 220 to acquire the facial image.

The first image acquisition unit 210 acquires a two-dimensional image by photographing the head of the patient whose face is to be corrected, and the second image acquisition unit 220 acquires a 3D facial image by photographing, more specifically by scanning the face of the patient.

The first image acquisition unit 210 and the second image acquisition unit 220 may be implemented separately from each other and connected to a computer in which a program is executed to implement the method for providing a face adjustment image, or may be configured as a single device and connected to the above computer as a composite image photographing device.

The first image acquisition unit 210 may acquire the cephalometric image by X-ray photography. The cephalometric image may have an image of osseous tissues (a cranium image and a teeth image), and the soft skin tissues of the face may form a relatively transparent outline compared to the osseous tissues on the surface of the osseous tissue image due to the difference in X-ray absorption.

The matching module 120, namely the matching unit, may generate a matched image by superimposing the cephalometric image and the facial image stored in the image storage module 141 of the data storage unit 140. The image storage module 141 may receive and store the cephalometric image and the facial image transmitted from the first image acquisition unit 210 and the second image acquisition unit 220, and may also store various images such as the matched image and the predicted facial image.

The image display module 130 displays a predicted facial image on a screen based on the change in the soft skin tissues in the matched image. More specifically, the image display module 130 displays the predicted facial image based on the change in the soft skin tissues according to the skeletal change in the cephalometric image. Moreover, the image display module 130 displays the images such as the cephalometric image, the facial image, the matched image, and the predicted facial image by simulation steps on the screen of a computer, a terminal or the like.

The matching module 120 enables the computer to function as matching means, image generation/display means and image storage means in cooperation with the image display module 130 and the image storage module 141. Further, the interface display module 150 displays a user interface on the screen to generate the face adjustment image. The control unit 110 controls the above modules to process the face adjustment image.

Figure 10:
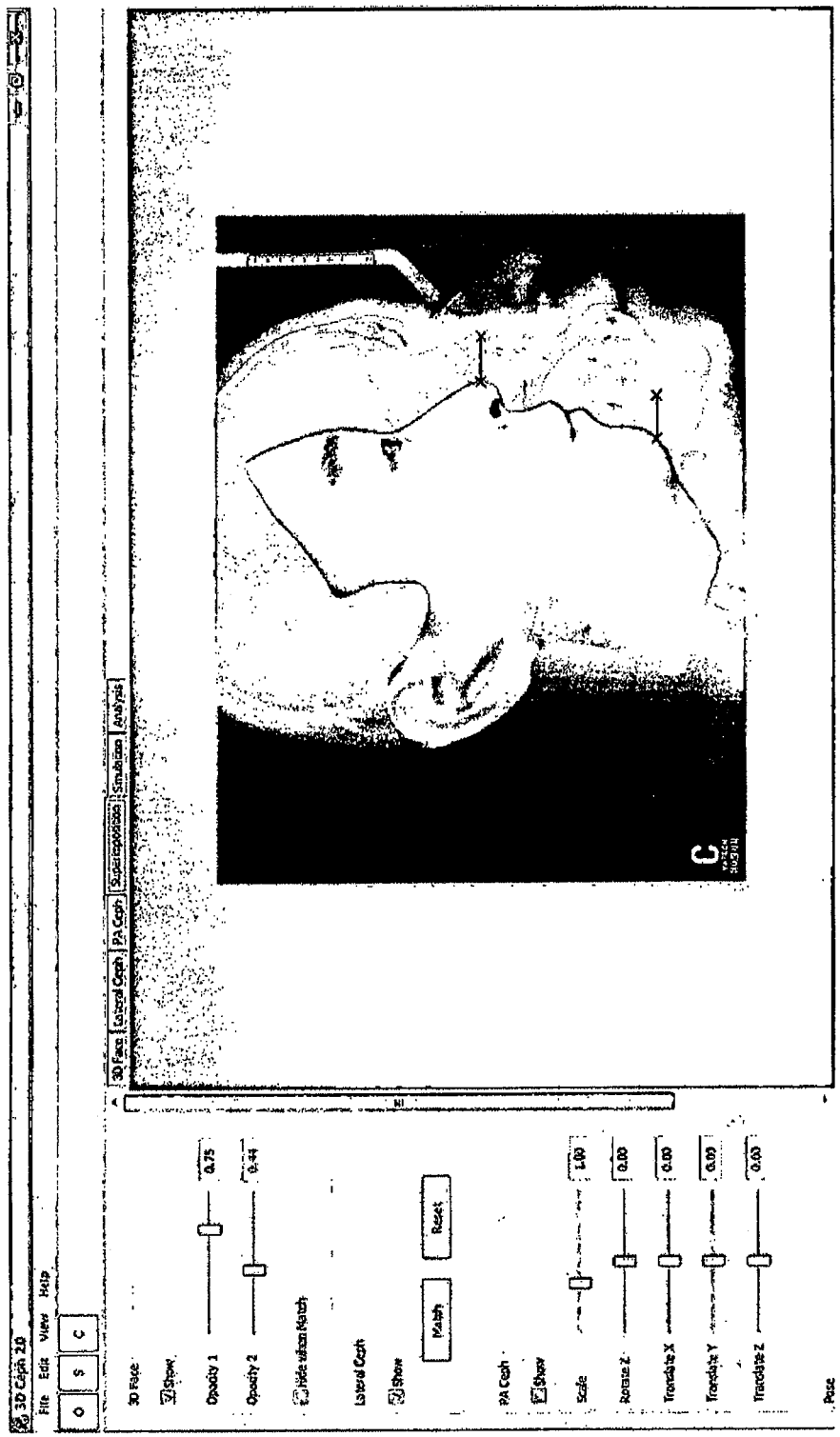
FIG. 10 is a captured image of a display window showing the procedures to arrange the counterpart points of the cephalometric image and the 3D facial image.
Figure 11:
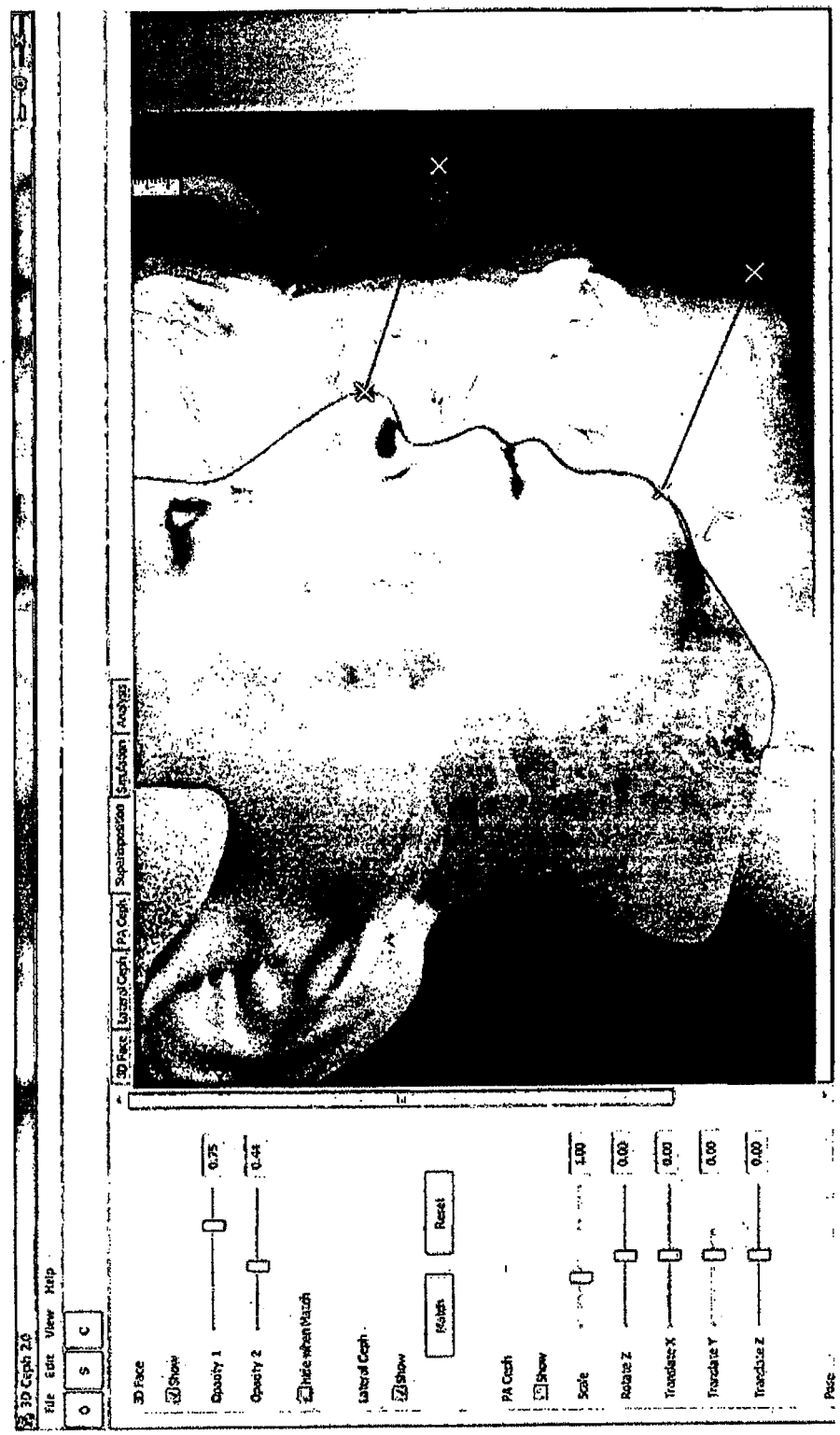
FIG. 11 is a captured image of a display window showing the procedures to adjust the size and orientation of the cephalometric image and the 3D facial image.
Figure 12:
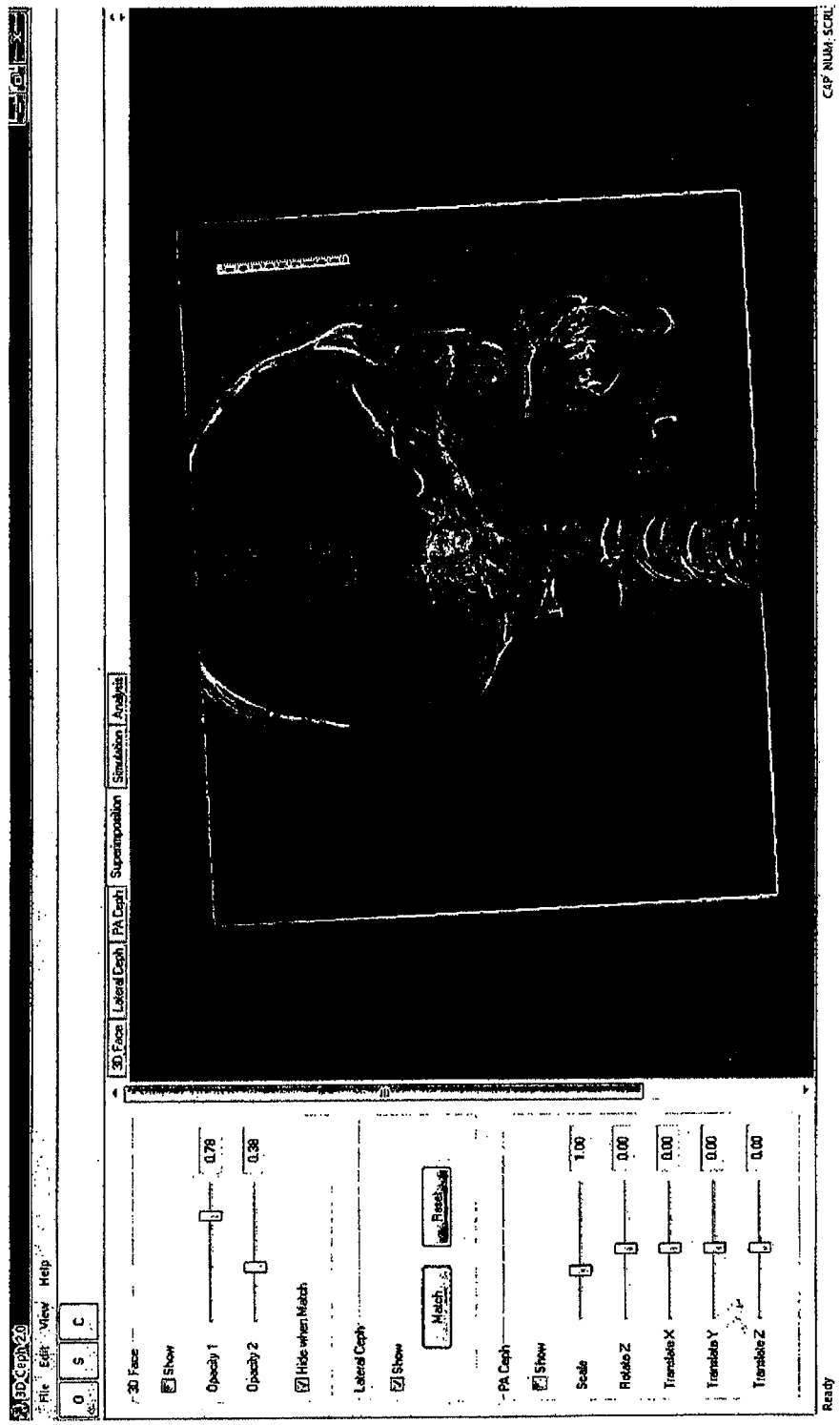
FIG. 12 is a captured image of a display window showing a matched image in which the 3D facial image excluding the profile line is displayed transparently.

Meanwhile, the step (a) (S120), namely the matched image generation step, superimposes the facial image and the cephalometric image by matching a plurality of first alignment points arranged on the facial image (See FIGS. 10 and 11) and a plurality of second alignment points arranged on the positions corresponding to those of the first alignment points on the outline of the cephalometric image (See FIGS. 10 and 11).

The first alignment points are arranged on the facial image to superimpose the facial image and the cephalometric image, and the second alignment points are arranged on the positions corresponding to those of the first alignment points on the cephalometric outline, which forms the edge of the cephalometric image by the soft skin tissues.

In other words, the first alignment points and the second alignment points are arranged so that they are located on the same parts of the face. For example, when the first alignment points are arranged on the tips of the nose and the jaw in the facial image, the second alignment points are also arranged on the tips of the nose and the jaw in the cephalometric image.

Therefore, the step (a) (S120) may comprise the steps of: (a1) receiving inputs for the first alignment points and the second alignment points (S110) (i.e., the alignment point input step), and (a2) generating and displaying the matched image on the screen in which the facial image is superimposed with the cephalometric image (S120) (i.e., the matched image display step).

Preferably, the step (a) (S120) further comprises the step of (a3) adjusting the size and orientation of the cephalometric image to the same as those of the facial image (S130) (i.e., the image adjustment step) because the size and orientation of the cephalometric image may differ from those of the facial image.

More specifically, the first alignment points comprise a pair of facial alignment points such as the pronasale (the first pronasale) and the gnathion (the first gnathion) on the facial image, and the second alignment points comprise a pair of outline alignment points such as the pronasale (the second pronasale) and the gnathion (the second gnathion) on the cephalometric image, which are arranged on the positions corresponding to the facial alignment points, i.e., on the same positions of the face.

Further, the step (a3) (S130) is performed by matching the size and orientation of a first vector formed by the facial alignment points and a second vector formed by the outline alignment points.

The step (a) (S120) may further comprise the step of (a4) displaying matching alignment lines on the screen (S140). The alignment lines are respectively formed on the first alignment points before the step (a1) (S110), and their orientations and lengths may be adjusted to achieve one-to-one correspondence of the first alignment points to the second alignment points (See FIGS. 10 and 11).

Therefore, the user may use a user interface such as a mouse to click and drag the end points of the alignment lines to match with the second alignment points, so that the matching module 120 may move at least one of the cephalometric image and the facial image to superimpose the cephalometric image and the facial image exactly.

Figure 3:
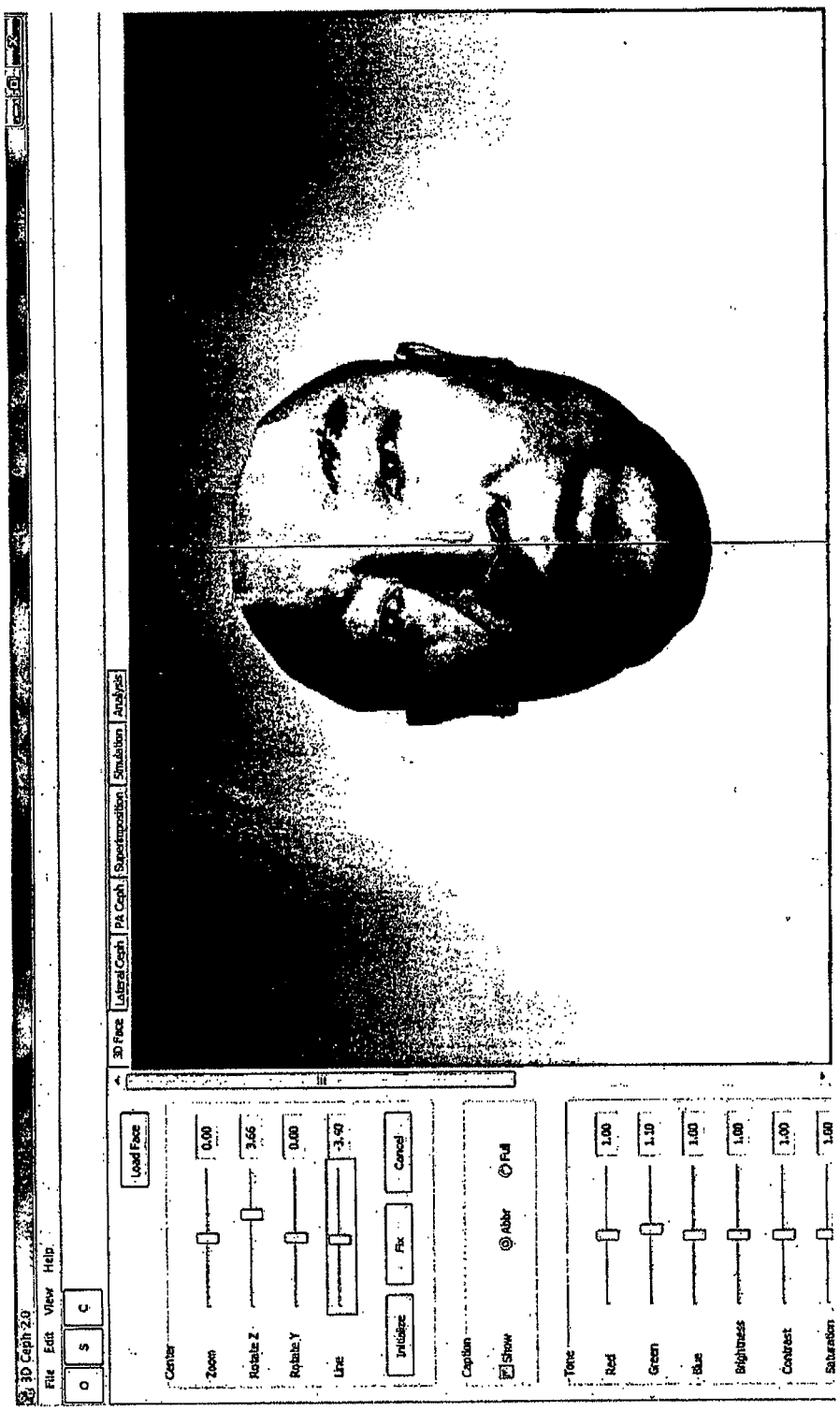
FIG. 3 is a captured image of a display window (screen) showing the front side of a 3D facial image.

In the present embodiment, the step (a) (S120) generates the matched image by superimposing the cephalometric image on the cross section of the facial image divided by the matching reference line arranged on the facial image (See FIGS. 2 and 3).

The matching reference line herein is a vertical line dividing the facial image to the left and right sides, and the cephalometric image may be a lateral cephalometric image obtained by photographing the head of the patient on the lateral side perpendicular to the front side of the face.

Further, in the step (a) (S120), particularly in the matched image display step (a2) (S120), one of the two lateral sides of the facial image divided by the cephalometric image may be displayed transparently on the screen so that the cephalometric image may be displayed on the screen.

Next, the step (b) (S130), namely the predicted image display step, is a step of displaying a predicted facial image, which is implemented based on the transformation of soft skin tissues in the matched image, on a screen. More particularly, the step (b) (S130) is a step of displaying the predicted facial image on the screen by transforming the soft skin tissues according to the skeletal change in the cephalometric image.

In the present embodiment, the step (b) (S130) comprises the steps of (b1) determining the change in the soft skin tissues corresponding to the skeletal change in the head (S210), and (b2) displaying the predicted facial image on the screen based on the change in the soft skin tissues (S220).

The skeletal change in the head may refer to at least one of tooth migration and cranial transformation such as the transformation of jawbones (upper and/or lower jawbones), cheekbones, frontal bones or the like, and furthermore may result from prostheses implanted to the face to support the soft skin tissues (e.g., nasal implant). The step (b2) selectively displays contour lines for showing the change in the soft skin tissues on the predicted facial image (S220).

Further, in the step (b) of the method for providing a face adjustment image according to the invention (S130), the predicted facial images before and after the simulation may be displayed on the screen simultaneously or sequentially so that the user and/or the patient may compare the images before and after the simulation.

Hereinafter, the specific steps to implement the method for providing a face adjustment image according to the invention will be described in more detail.

1. 3D Facial Image

In the first step, the 3D face model acquired by a 3D scanner, namely the 3D facial image is loaded on a screen and the step of arranging the above-mentioned matching reference line or the like is performed.

Referring to FIG. 3, the user pushes the button to load the facial image (Load Face) in the user interface displayed on the screen by the interface display module 150, and then selects the 3D facial image data having the desired shape from the image data box so that the 3D face model, i.e., the facial image is displayed on the screen by the image display module 130.

In order to arrange the matching reference line, the facial image may be enlarged/reduced using a zoom function and rotated using a rotation function. To this end, the interface display module 150 displays a rotation bar, a zoom bar and a reference line track bar on one side of the screen, which are used to adjust the enlargement/reduction, Z-axis rotation (Rotate Z) and Y-axis rotation (Rotate Y) of the facial image as well as the matching reference line arrangement. The Rotate Z track bar rotates the facial image around the Z-axis (the horizontal or vertical axis of the screen), and the Rotate Y track bar rotates the facial image around the Y axis (the vertical or horizontal axis of the screen, perpendicular to the Z-axis). The Line track bar moves the blue line (matching reference line) to the left or right.

Meanwhile, the user may push the Initialize button on the screen to initialize the enlargement ratio and rotation of the facial image and the position of the matching reference line.

Figure 4:
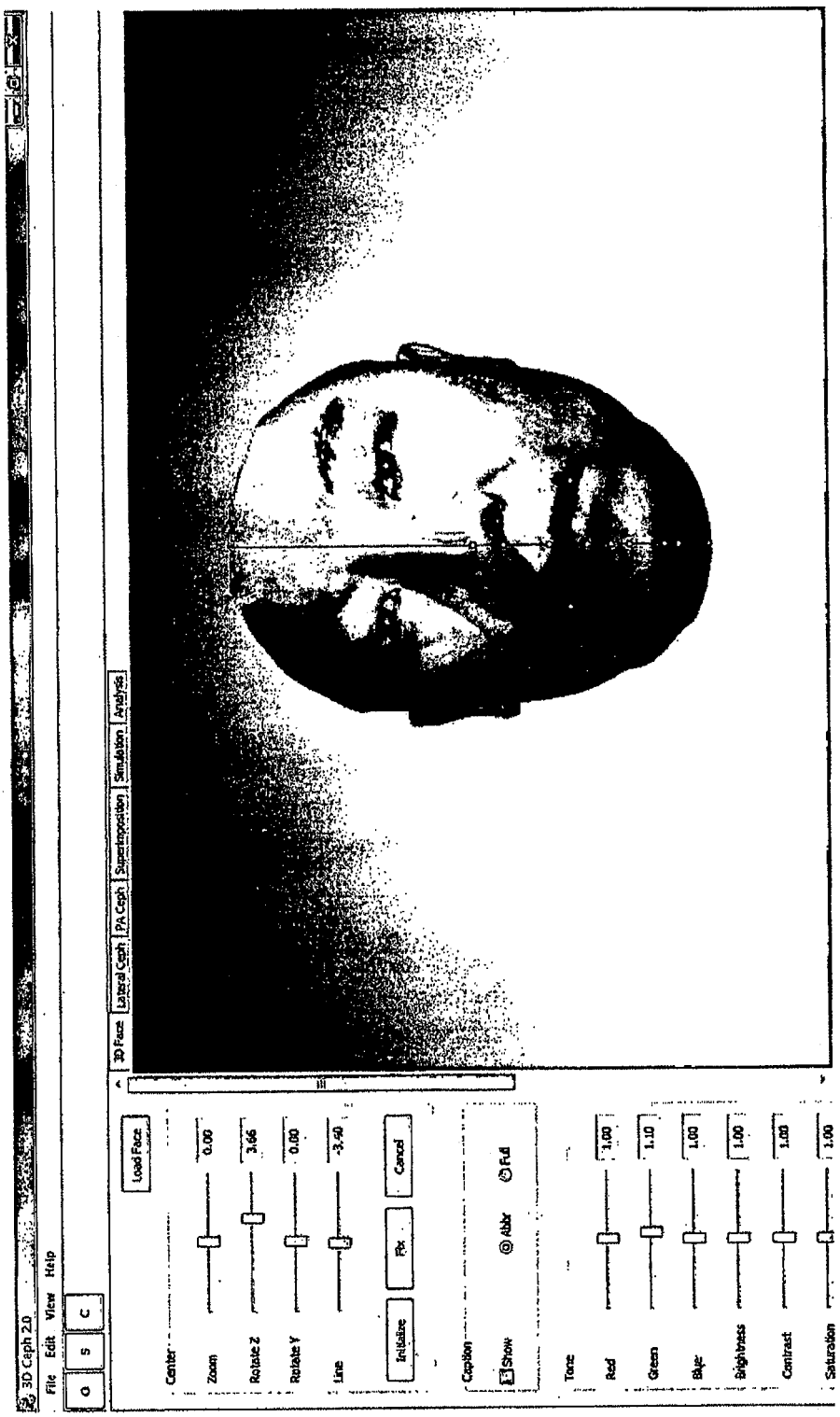
FIG. 4 is a captured image of a display window showing the feature points and the alignment reference line dividing the facial image to the left and right sides.
Figure 5:
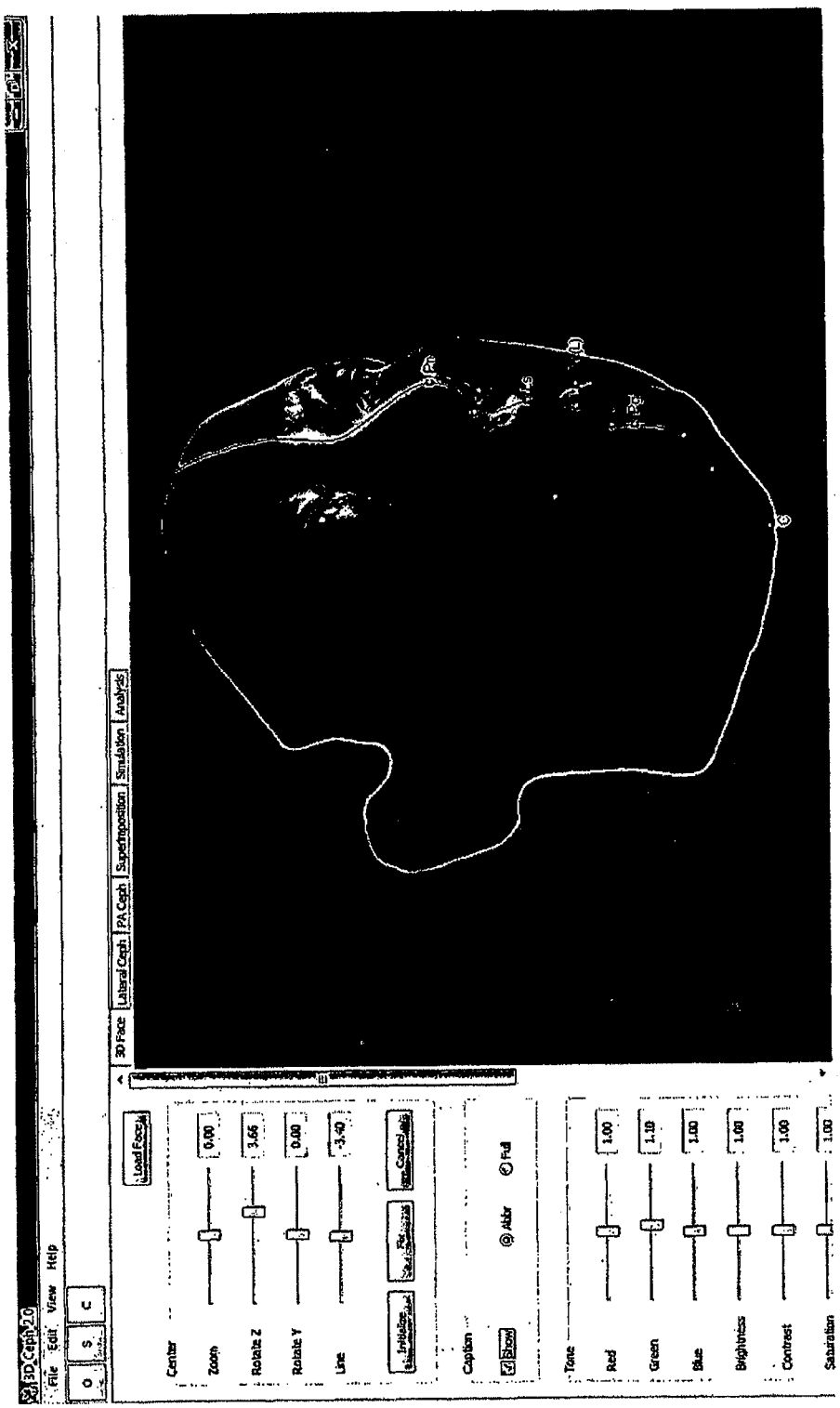
FIG. 5 is a captured image of a display window showing a 3D facial image in which the profile according to the alignment reference line is displayed.

Referring to FIGS. 4 and 5, when the Fix button is pushed after the matching reference line is arranged, the two-dimensional matching reference line is projected on the 3D facial image so that the image display module 130 display the Profile line (e.g. red line) automatically, and the facial feature points such as pronasale, gnathion, cheilion and the like may be automatically displayed as small dots on the screen simultaneously with or subsequently to the generation of the Profile line. The locations of the feature points may also be manually designated or corrected by the user. The principles to detect the feature points in the facial image will be illustrated below.

The 3D face model, i.e., the 3D facial image is generally comprised of meshes and texture images, and the control unit 110 analyzes the geometric information of the meshes and the image information of the textures to automatically extract the feature points. For example, the pronasale may be detected by searching for the most protrusive point on the profile line in the face; the cheilion may be detected by analyzing the color distribution of the texture images (skin color and lip color area) to obtain the lip area and then find both ends of the lip area; and the gnathion may be detected by finding the lower end point in the face where the facial outline meets the profile line. The reason to detect the feature points will be described below.

The feature points can be used to analyze the face condition of the patient. More specifically, by connecting the feature points to generate the lines, the lengths or angles of the specific parts of the face (e.g. the width of the lip, the occlusion angle between the upper and lower lips, or the like) may be detected and compared to the existing average values to analyze and diagnose the face condition of the patient.

Further, the feature points may be used as the matching reference points, i.e., the alignment points of the 3D facial image and the cephalometric image. For example, two feature points on the 3D face model such as pronasale and soft-tissue gnathion may be used as the matching reference points of the two-dimensional facial image and the cephalometric image.

Moreover, in order to adjust the up-down slope of the 3D facial image, the feature points may be used to arrange the nose-chin line, i.e., the slope line to be described below. The slope line is generated by connecting pronasale with soft-tissue gnathion, particularly soft-tissue pogonion. The feature points may be stored in a database or the data file 140 in the form of coordinate values based on the virtual coordinates on the screen. The lengths or angles of the specific parts of the face may be determined by calculating the coordinate values.

Further, the user may operate the image display module 130 using a mouse to rotate the facial image on the screen to check the formation of the profile line on the 3D facial image as shown in FIG. 5, and optionally to display the names of the feature points on the 3D facial image. The color, brightness, contrast and the like of the facial image may be adjusted to change and display the tone of the facial image.

2. Cephalometric Image

Before or after the 3 D facial image processing, the cephalometric image is loaded on the screen by the image display module and then the landmark points are displayed on the cephalometric image on the screen.

Figure 6:
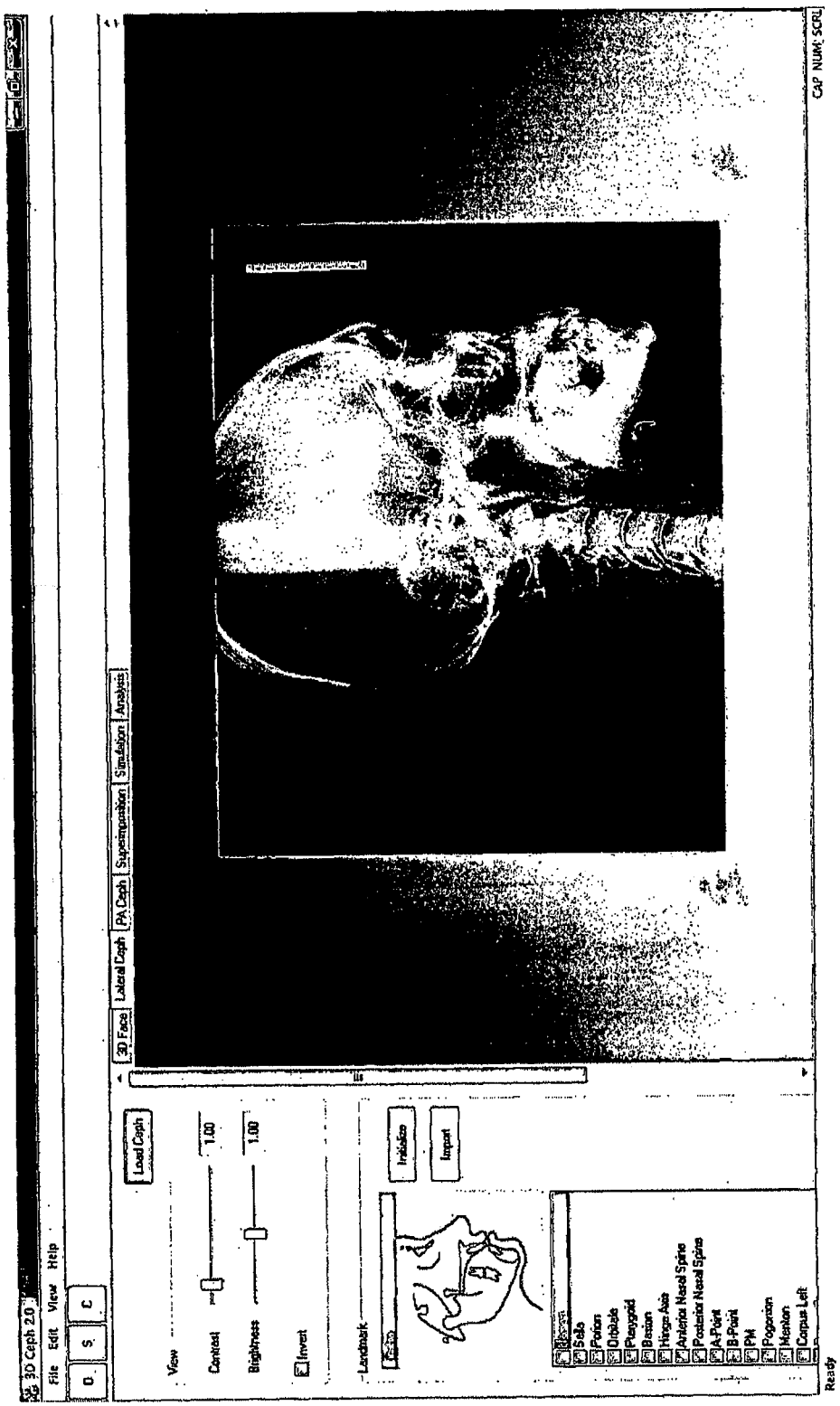
FIG. 6 is a captured image of a display window showing a lateral cephalometric image as one example of a cephalometric image.
Figure 7:
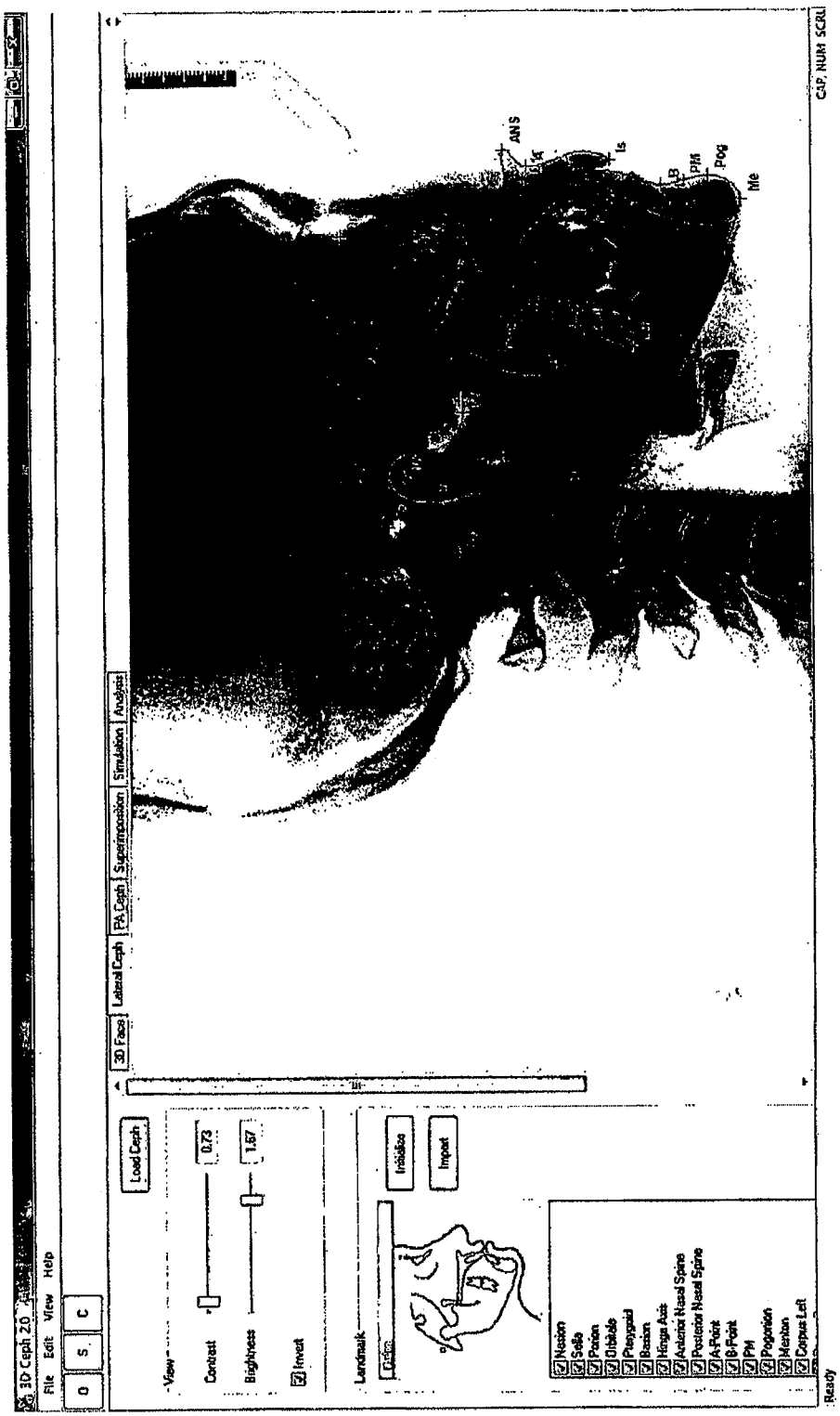
FIG. 7 is a captured image of a display window showing a cephalometric image in which the landmark points and the landmark lines are displayed.

FIGS. 6 and 7 show that the lateral cephalometric X-ray image is displayed on the screen as one example of the cephalometric image, which is an X-ray image taken from the lateral side perpendicular to the front side of the face. Upon loading the cephalometric image on the screen, the contrast and brightness of the cephalometric image may be adjusted, and the cephalometric image may be displayed with black and white inverted when the Invert checkbox is checked.

When the user manually clicks a certain spot of the cephalometric image using a mouse, the image display module may display on the screen a landmark point formed at the spot, which has a predetermined shape such as a blue cross shape, while the landmark points may be automatically arranged and displayed. Further, the landmark points can be moved or deleted.

The coordinate values of the landmark points are stored in a database or the data file 140 together with the coordinate values of the feature points.

Meanwhile, in a specific part of the cephalometric image, a model corresponding to the specific part may automatically appear by way of some of the landmark points. For example, upon arranging the locations of the landmark points on the teeth, the corresponding teeth model may be automatically displayed on the cephalometric image.

More specifically, in case of maxillary incisors, for example, when the user arranges two landmark points at the root apex and the crown tip of the maxillary incisors displayed on the cephalometric image, respectively, the size, location, and rotation value of a maxillary incisor model having a predefined shape connecting the landmark points (e.g. the outline of the maxillary incisor shape) will be converted based on the distance and angle between the root apex and the crown tip so that the model may be superimposed with the maxillary incisors of the cephalometric image.

Further, if a plurality of auxiliary points are manually arranged among the landmark points using a mouse so that the landmark points are smoothly connected, then a landmark line smoothly connecting the landmark points via the auxiliary points is displayed on the screen.

The coordinates of the landmark points may be stored in a data storage unit such as a database, the data file 140 or other memory units. If the user presses the Initialize button in the tool box, which is displayed on the right side of the screen by the interface display module 150, then all the previously arranged landmark points and lines are erased so that the work may be restarted from an initial state.

The formation of the landmark points and lines may allow the analysis on the head of the patient. The landmark lines may roughly depict the locations and shapes of the maxilla, mandible and the like. Further, a simulative operation may be performed by moving the locations of the maxilla and mandible or cutting a part of the maxilla and mandible. Moreover, by directly connecting the landmark points or generating auxiliary lines extended from the landmark points, the shapes of various parts such as maxilla, mandible, or chin line as well as the lengths and angles between the specific points may be detected. The detected data may be subjected to an analysis work comparing the data with existing average values to diagnose/analyze the condition of the patient.

Figure 8:
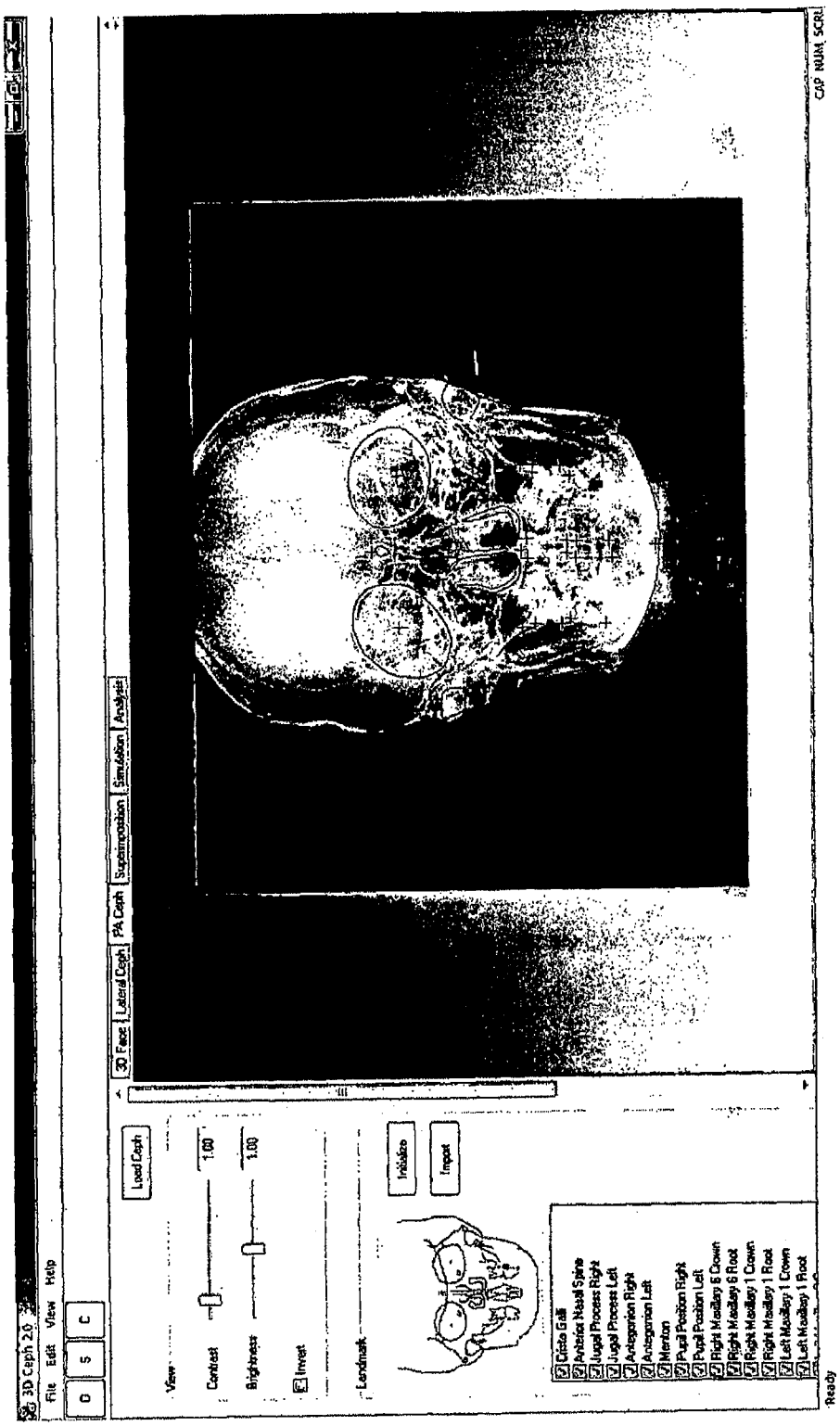
FIG. 8 is a captured image of a display window showing a front cephalometric image as one example of a cephalometric image.

Meanwhile, FIG. 8 shows an X-ray image taken from the front side of the face, i.e., a front cephalometric image, as another example of the cephalometric image. The generation and display of the above-mentioned landmark points and lines may be also performed with the front cephalometric image. For example, if the target area for the face correction is the left and right chin lines of the mandible, then the front cephalometric image may be used to perform a simulative face correction operation.

3. Generating a Matched Image (Superimposition)

Referring to FIGS. 9 to 13, the matching module 120 performs the step of superimposing the 3D face image and the cephalometric image on 3D coordinates and aligning the superimposed image on the screen, as a procedure to implement the present invention.

The facial image is a three-dimensional object in a 3D space, while the cephalometric image is a two-dimensional object on a two-dimensional plane. In order to superimpose the two images on a common 3D coordinate space, the facial image and the cepahlometric image are superimposed so that the cephalometric image such as the above-mentioned lateral cephalometric image is placed on the plane passing the profile line of the 3D facial image and dividing the face in a bilaterally symmetric way.

Figure 9:
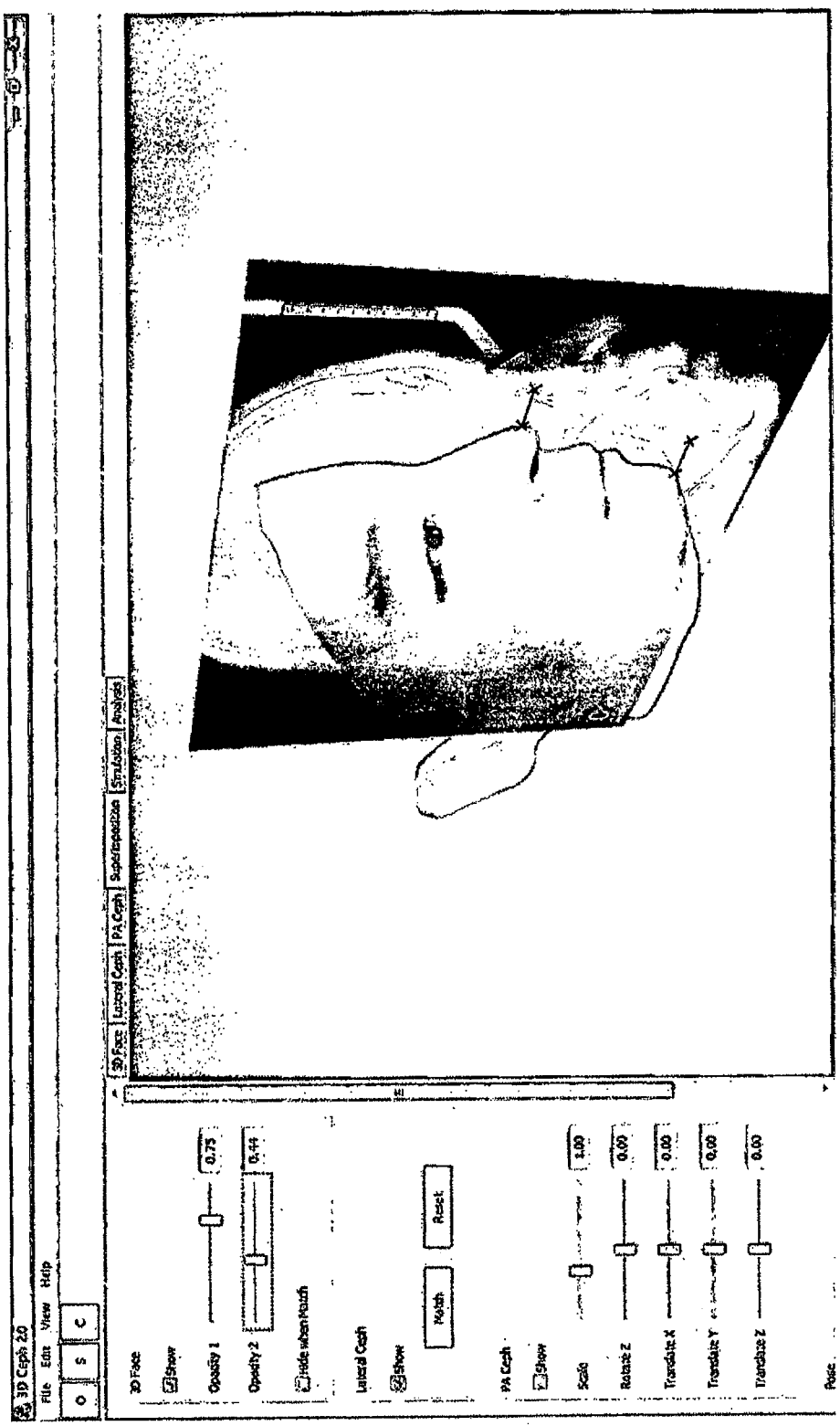
FIG. 9 is a captured image of a display window showing a cephalometric image and a 3D facial image simultaneously to superimpose the cephalometric image and the 3D facial image.

The screen in FIG. 9 shows that the 3D facial image and the cephalometric image are simultaneously displayed in the common 3D coordinate space on the screen as described above. The screen may be adjusted using the following interface tools in the tool box on the right side of the screen.

(1) Opacity 1: adjusts the transparency of the entire 3D facial image.

(2) Opacity 2: adjusts the transparency of the farther one (from the user) of the two parts of the 3D facial image divided by the middle plane.

(3) Contrast: adjusts the contrast of the cephalometric image.

(4) Brightness: adjusts the brightness of the cephalometric image.

(5) Invert: inverts the black and white of the cephalometric image.

Referring to FIGS. 10 and 11, the 3D facial image and the cephalometric image displayed in the common 3D coordinate space on the screen may differ in their size and location, and their rotation value (the degree of lowering the head observed from the lateral side; referred to as "facial slope" hereinafter) may also differ.

To match the size, location and rotation value of the 3D facial image and the cephalometric image, the scale, rotation and translation values (hereinafter "SRT values") of one of the two images are to be adjusted. In the present embodiment, the size, location and rotation value of the cephalometric image are adjusted with respect to the 3D facial image. However, the present invention is not limited thereto.

In this embodiment, to increase the accuracy of superimposing the facial image and the cephalometric image, there is provided a method for arranging a plurality of counterpart points (e.g. two pairs of counterpart points) in the 3D facial image and the cephalometric image and matching them.

The counterpart points comprise a plurality of first alignment points arranged on the facial image and a plurality of second alignment points arranged on the cephalometric image. As shown in FIGS. 10 and 11, if the cephalometric image is the lateral cephalometric image, the second alignment points are located on the edge (i.e., outline) of the lateral cephalometric image formed by the soft skin tissues, and arranged on the positions corresponding to those of the first alignment points.

In other words, the first alignment points and the second alignment points are arranged on the same spots of the face in the facial image and the cephalometric image. In this embodiment, a pair of facial alignment points are provided as the first alignment points and a pair of outline alignment points are provided as the second alignment points.

More specifically, the pronasale and gnathion in the facial image and the cephalometric image are respectively selected as two pairs of the counterpart points in this embodiment. The pronasale and gnathion of the 3D facial image become the facial alignment points, and the pronasale and gnathion of the cephalometric image become the outline alignment points. However, the alignment points are not limited thereto, and other parts such as philtrum or glabella may be designated as the alignment points. The coordinate values of the second alignment points, i.e., the pronasale and gnathion are stored in the data storage unit 140 such as a data file or a database.

Further, a first vector connecting the pronasale and gnathion of the 3D facial image and a second vector connecting the pronasale and gnathion of the cephalometric image are generated using the coordinate values of the pronasale and gnathion, and then the size and orientation of the first and second vectors are matched so that the SRT values of the facial image and the cephalometric image are the same.

The locations of the pronasale and gnathion of the 3D facial image may be arranged by extracting the feature points as described above. More specifically, those locations are arranged on the two feature points located on the matching reference line, e.g., the two locations of the pronasale and gnathion on the cephalometric image.

In this embodiment, the alignment points are indicated as 'X' on the pronasale and gnathion on the 3D facial image, and each matching alignment line formed extending protrusively from each alignment point may be displayed on the screen. The matching points are respectively indicated as 'X' in another color (e.g. red) at the tips of the matching alignment line. The orientation and length of the matching alignment line can be adjusted so that the user may change the length and orientation of the alignment line by clicking/dragging each matching point with a mouse. By locating the matching points of the matching alignment line on the pronasale and gnathion of the cephalometric image, respectively, the matching location reference of the two images is established. The matching alignment line is provided herein to facilitate intuitive understanding of the user, and simply finding the locations of two pairs of counterpart points actually allows establishing the matching location reference of the two images.

As described above, if the Match button on the screen is pressed after properly connecting the corresponding pronasale and gnathion, then the size, location and rotation value of the cephalometric image are adjusted to match with those of the facial image, and the cephalometric image and the 3D facial image are correctly superimposed.

Figure 13:
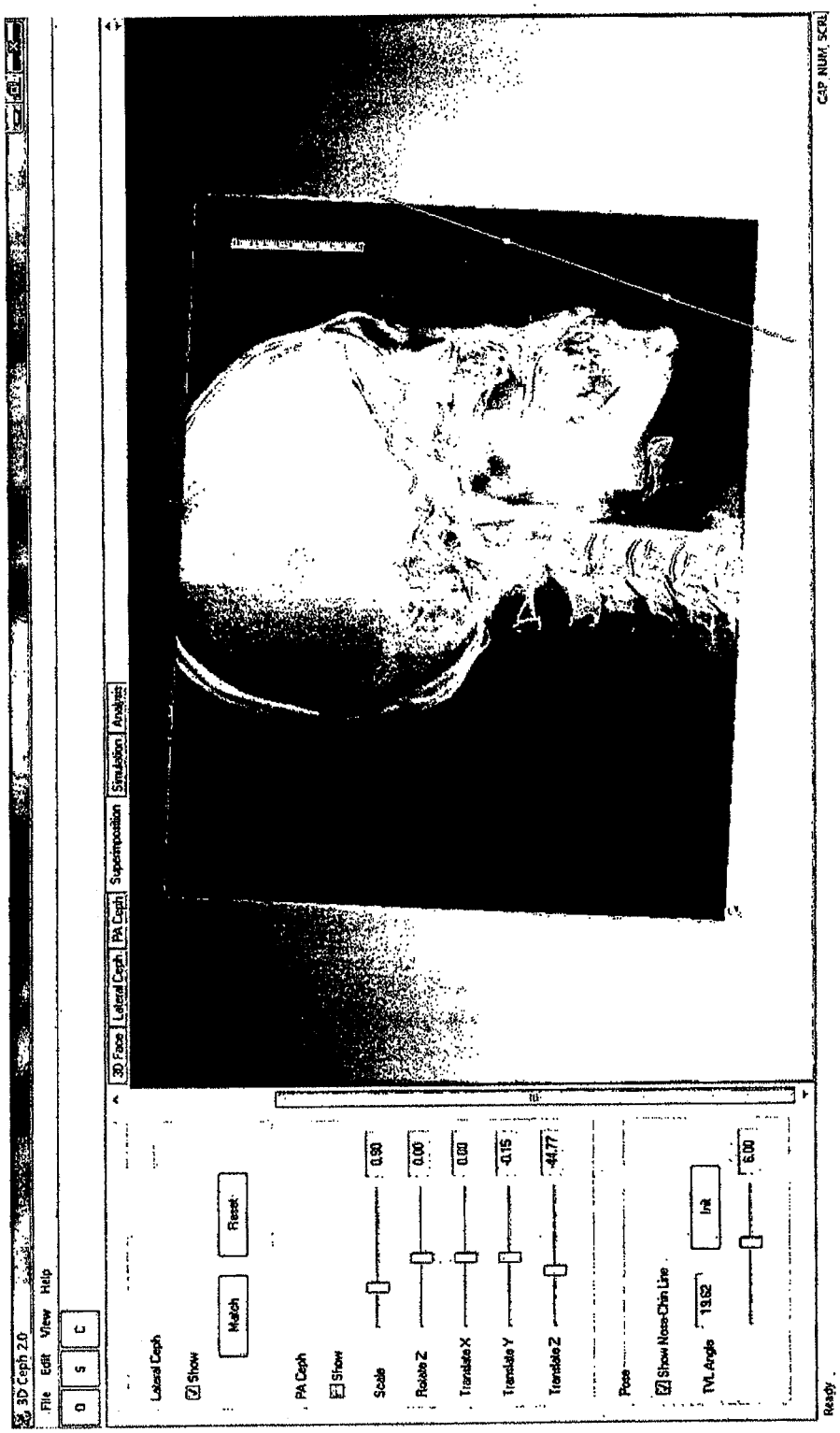
FIG. 13 is a captured image of a display window showing the procedures to arrange the slope angle of the matched image.

Meanwhile, the remaining parts in the facial image except the profile line may be processed to become transparent so that the cephalometric image and the matched image in which the profile line only remains may be selectively displayed on the screen as shown in FIG. 13. This makes it easier to determine the accuracy of superimposing the facial image and the cephalometric image. The image display module 130 may display the above images as the Opacity 1 track bar is adjusted.

Moreover, as shown in FIG. 13, the image display module may display the slope line connecting the pronasale and gnathion, and the angle between the slope line and the true vertical line (namely the true vertical line angle or TVL angle) may be also displayed. In this embodiment, the true vertical line is assumed to be a virtual line parallel to the vertical line of the screen, and the TVL angle may be adjusted to adjust the facial slope.

4. Displaying a Predicted Facial Image

Figure 14:
FIG. 14 is a captured image of a display window showing a half-cut matched image as one example of a matched image.

FIG. 14 shows a matched image in which the 3D facial image is exactly cut by the cephalometric image superimposed along the profile line of the 3D facial image, i.e., a half-cut matched image. Accordingly, superimposing the two-dimensional cephalometric image and the 3D facial image causes the internal skeletal structure of the face to look three-dimensional.

To this end, transparency adjustment means (Opacity track bar) may be used to adjust the transparency of the right half of the 3D facial image divided by the cephalometric image. The half-cut matched image may be rotated to the desired orientation by the user and then displayed. As shown in FIG. 14, the image display module 130 displays the half-cut matched image on the screen in the orientation as desired by the user.

Further, in the step (b), i.e., the predicted facial image display step (S130), the image display module 130 determines the change in the soft skin tissues corresponding to the skeletal change in the head and displays a predicted facial image on the screen based on the change in the soft skin tissues.

On the contrary, the change in the soft skin tissues may involve the skeletal change in the head (the change in the osseous tissue) so that the predicted facial image may be displayed on the screen. This may be performed by a method reverse to the method for determining the change in the soft skin tissues corresponding to the skeletal change in the head, and the principles to implement those methods are the same.

One example of the change in the soft skin tissues corresponding to the skeletal change in the head will be described below in more detail. When the user selects the Teeth checkbox on the right side of the screen, a teeth model, which is superimposed with the corresponding teeth part of the cephalometric image in the process of arranging the landmark points and lines of the cephalometric image, is shown in the form of the outline forming the edge of the teeth. When the user changes the location and orientation of the teeth model such as an upper/lower incisor model in the cephlometric image of the matched image using a mouse, the change in the soft skin tissues according to the change in the teeth model is displayed on the screen.

For example, when the user uses a mouse to click the landmark points arranged at the tips of the teeth crowns in the upper/lower incisor model and move them back and forth, the upper/lower lip parts move back and forth in a natural way according to the location change of the incisor model. In general, the degree of transformation of the upper/lower lip parts is proportional to the amount of movement of the tip of the incisor model. In this case, the most protrusive part of the lips (the center of the lips) is most transformed, and the degree of transformation decreases toward the up and down directions and both ends of the lips. In other words, if the transformed area of the soft tissues (e.g., the lip parts) changed in association with the movement of the upper incisor is predetermined and the rate of transformation of each part in the transformed area is determined, then the amount of transformation of the facial image is determined with reference to the transformation rates, and the facial image in which the soft skin tissues of the corresponding parts are changed based on the amount of transformation is displayed on the screen.

With respect to the change of the lips, the present invention determines the amount and area of change in the soft skin tissues (i.e., the lips) corresponding to the change in the location and orientation of the teeth. The operation data of various patients are stored in the data file 140, and the average values are derived based on the data. The transformation rate of the lips according to the amount of change in the tips of the teeth crowns is determined based on the average values, and the shape change in the lips is realized based on the transformation rate, thereby changing the facial image. The above transformation rate of the lips may be formularized and automatically calculated.

That is, the transformed parts and the amount of transformation (transformation rate) of the soft skin tissues may be determined based on the operation data of various patients, or the amount of transformation of the soft skin tissues may be automatically calculated according to a predetermined formula (parameter values may be inputted from the user). Otherwise, both of the above can be implemented in combination.

For example, if there exist operation data on the transformed parts of the soft skin tissues, then the control unit 110 may derive the amount of transformation using the operation data or determine those of the parts having no operation data according to a suitable formula.

As a specific example, the labrale superius/labrale inferius are most transformed by the movement of the maxillary/mandibular incisors. The amount of transformation of those parts may be calculated as (movement amount of the tip of the upper/lower incisor model)*(transformation rate inputted by the user or derived based on the operation data).

Further, the entire transformed area may be determined based on the feature points. When the maxillary/mandibular incisors move, the changed area of the soft skin tissues may be the area from the subnasale to the pogonion in the vertical direction and the area within a predetermined distance from the right/left cheilion in the horizontal direction. However, the transformed parts of the soft skin tissues may be altered based on the results of various clinical experiments, i.e., the operation data.

The degree of transformation decreases from the labrale superius/labrale inferius, which involve the most transformation among the soft skin tissues, toward the up and down directions and both ends of the lips. For example, a sine function can be used to determine the decrease in the degree of transformation, which is simple but effective.

Using the above method, when the skeleton of the specific part such as the teeth area is changed, the parts of the soft skin tissues changed in association with the skeletal change and the local transformation rates thereof may be determined and realized using the method for providing a face adjustment image according to the invention. Based on the above, three-dimensional transformations in the face can be displayed in a virtual image.

Figure 15:
FIG. 15 is a captured image of a display window showing the simulation procedures to generate a predicted facial image using a matched image.
Figure 16:
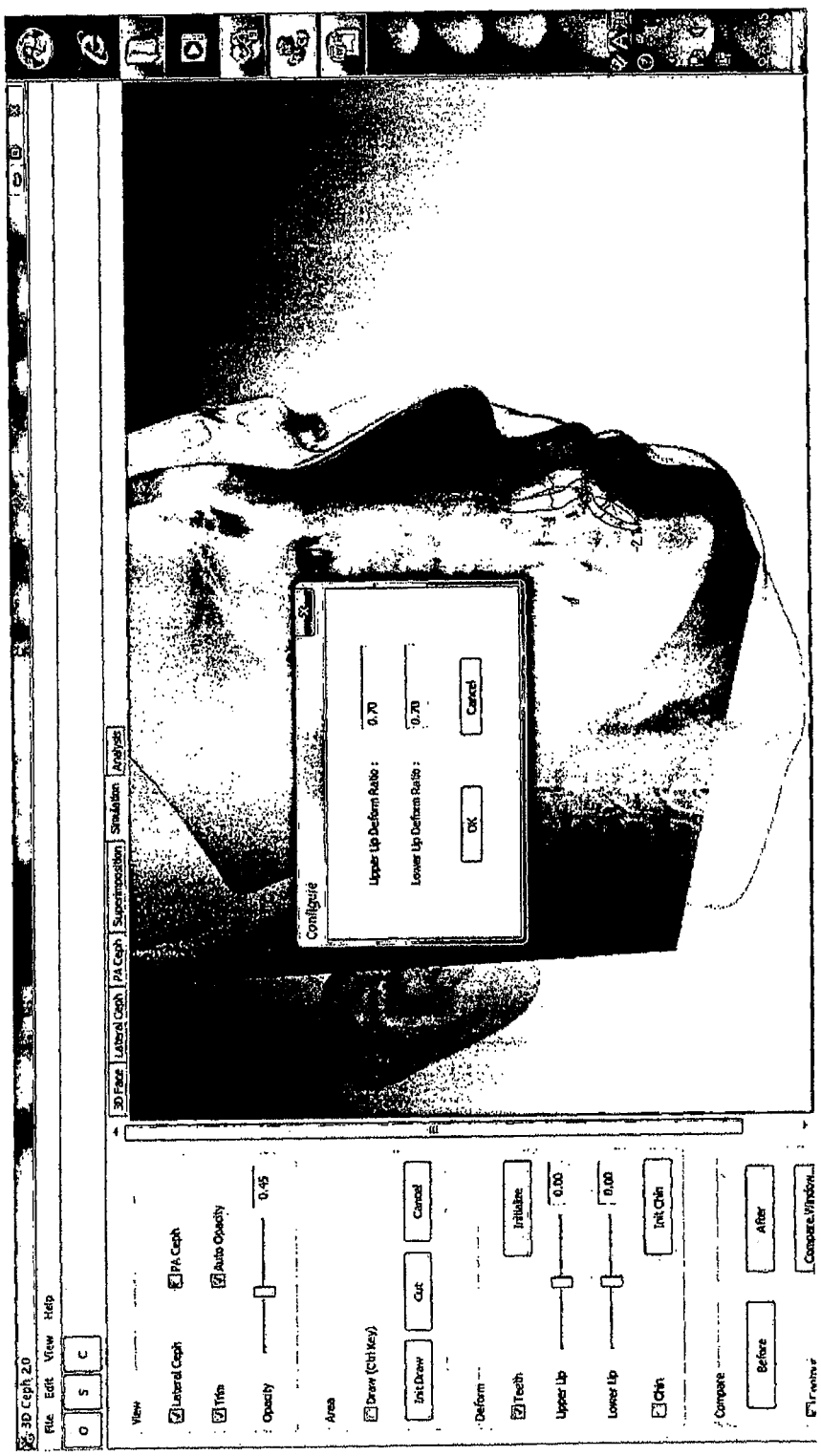
FIG. 16 is a captured image of a display window showing an input window in which the change rate of soft skin tissues may be manually inputted.

The transformation rate of the lips according to the change in the teeth model can be also inputted from the user through the input window as shown in FIG. 15, because each operator relies on different theories and criteria on the transformation rates and those rates may be slightly changed depending on the characteristics of each patient such as the lip height.

When the parts other than the teeth such as cheekbones are changed, the area of the soft tissues transformed in association with the change in the cheekbones and the local transformation rates thereof are determined in a separate way.

Figure 17:
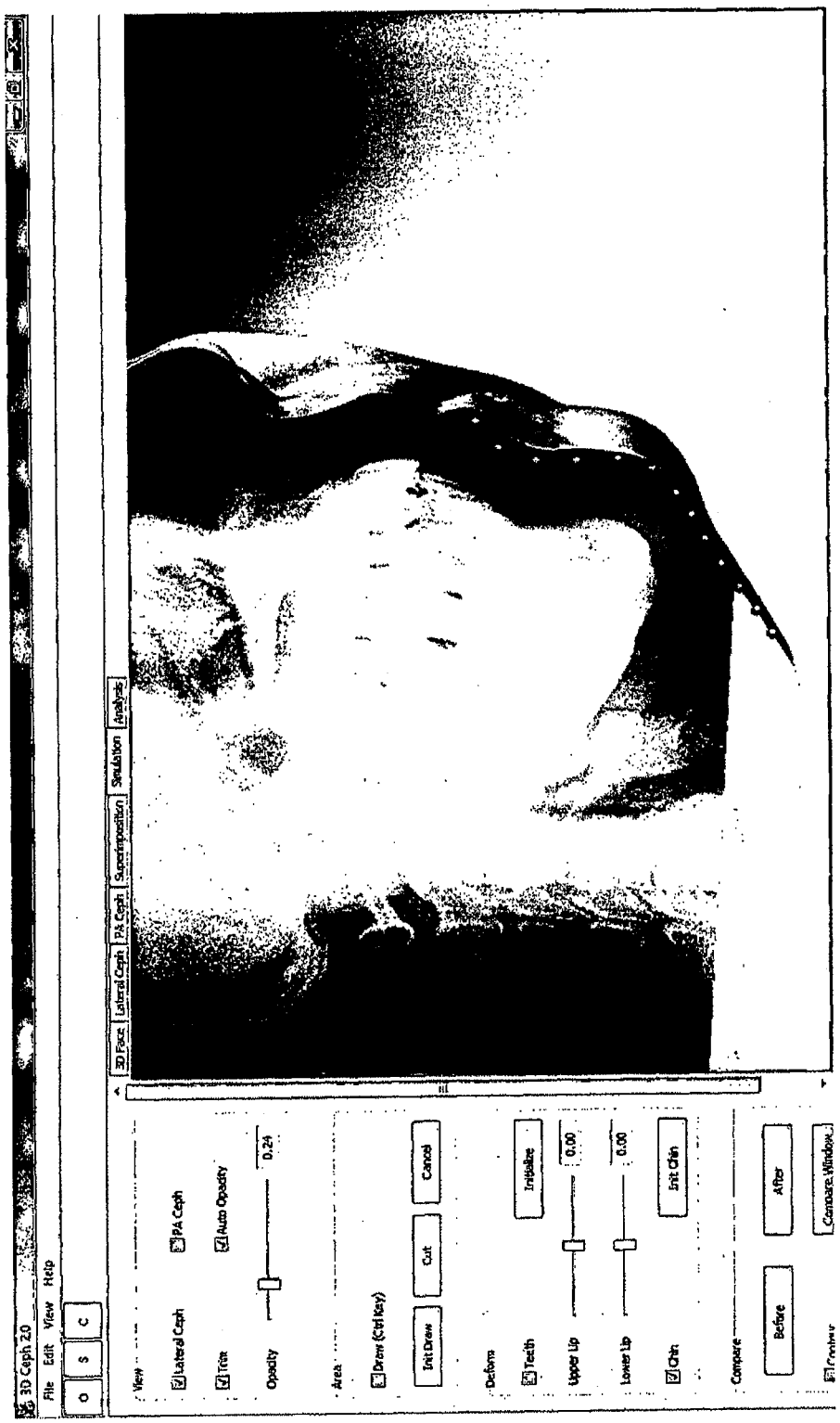
FIG. 17 is a captured image of a display window showing the procedures to correct a mandibular profile line.
Figure 18:
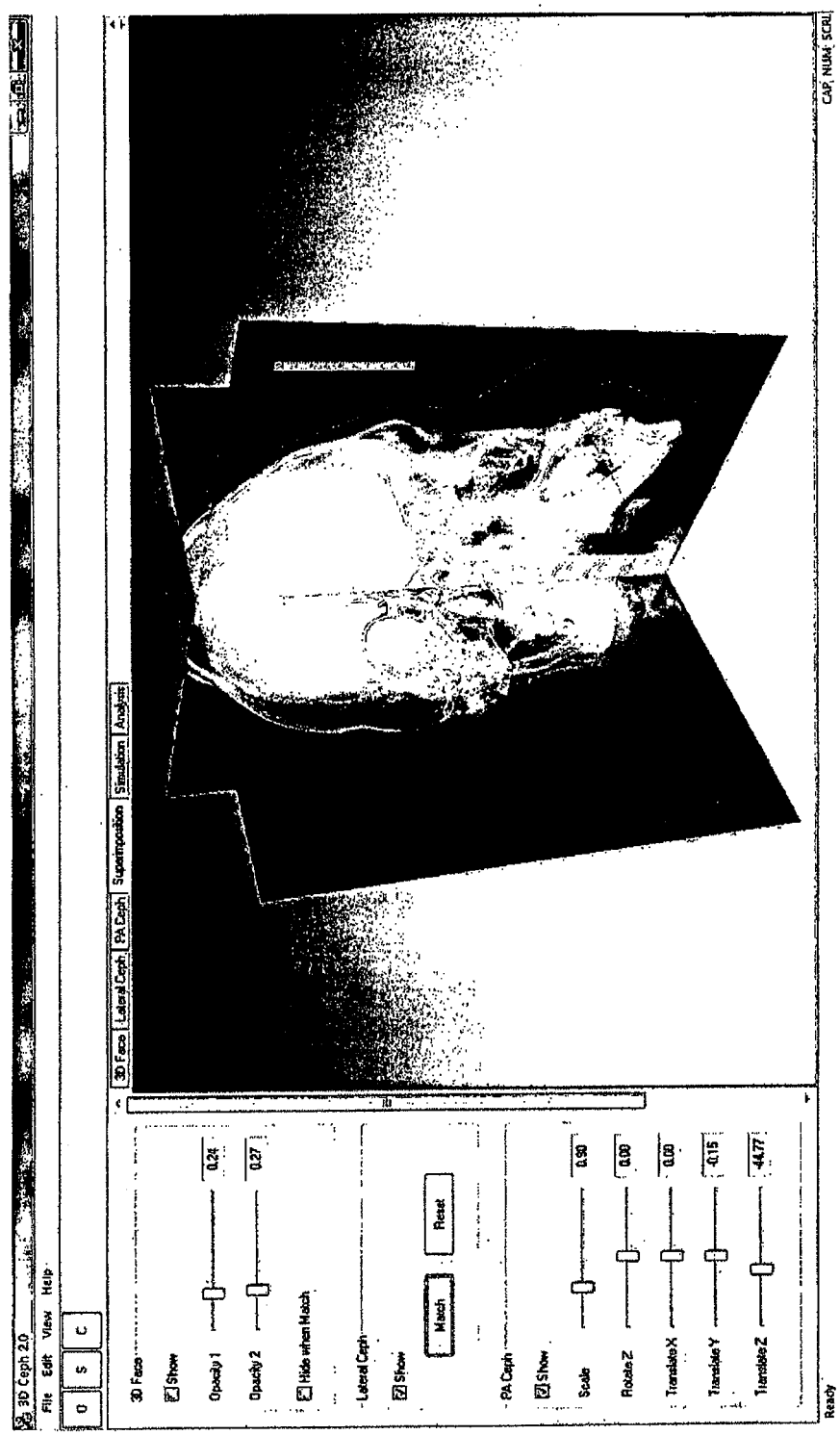
FIG. 18 is a captured image of a display window showing the superimposed state of a front cephalometric image and a lateral cephalometric image.

As shown in FIG. 17, the Upper Lip track bar and the Lower Lip track bar on the right side of the screen may be adjusted to move the locations of the upper and lower lips in the vertical direction, respectively, and display them on the screen.

According to the present invention, a simulation may be performed to correct the line that connects from the tip of the lower lip to the neck, and the locations of multiple control points placed on the line may be moved using a mouse to modify the shape of the line so that the shape of the jaw may be modified in a natural way to create an optimal face shape.

Meanwhile, the image display module 130 may display the matched image on the screen in which the lateral cephalometric image and the front cephalometric image are superimposed perpendicular to each other, and such images may be selectively displayed. That is, the lateral cephalometric image is rotated by a predetermined angle and then displayed on the screen, while the front cephalometric image is rotated to cross the lateral cephalometric image at a right angle and then displayed on the screen. At this time, the front cephalometric image is divided into two parts by the lateral cephalometric image, and the front cephalometric image may be superimposed with the 3D facial image and the lateral cephalometric image. The transparency of the 3D facial image may be adjusted to show only the front and lateral cephalometric images on the screen.

Figure 19:
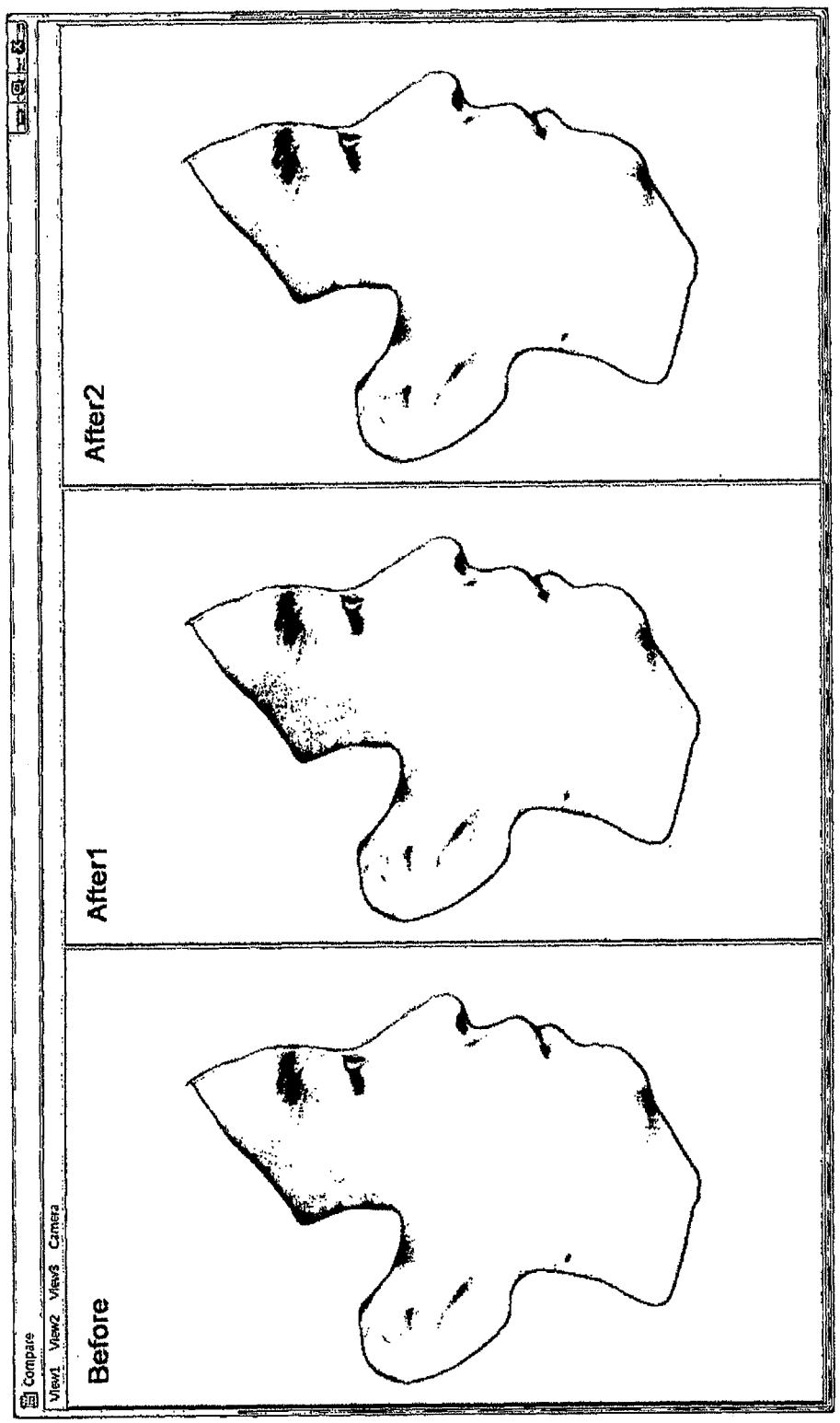
FIG. 19 is a captured image of a display window showing lateral facial images before and after an operation.

Next, referring to FIG. 19, the image display module 130 may display in the step (b) the appearances before and after the simulation. That is, the appearance before the operation and the predicted facial image may be displayed on the screen, simultaneously or sequentially, for comparison.

Figure 20:
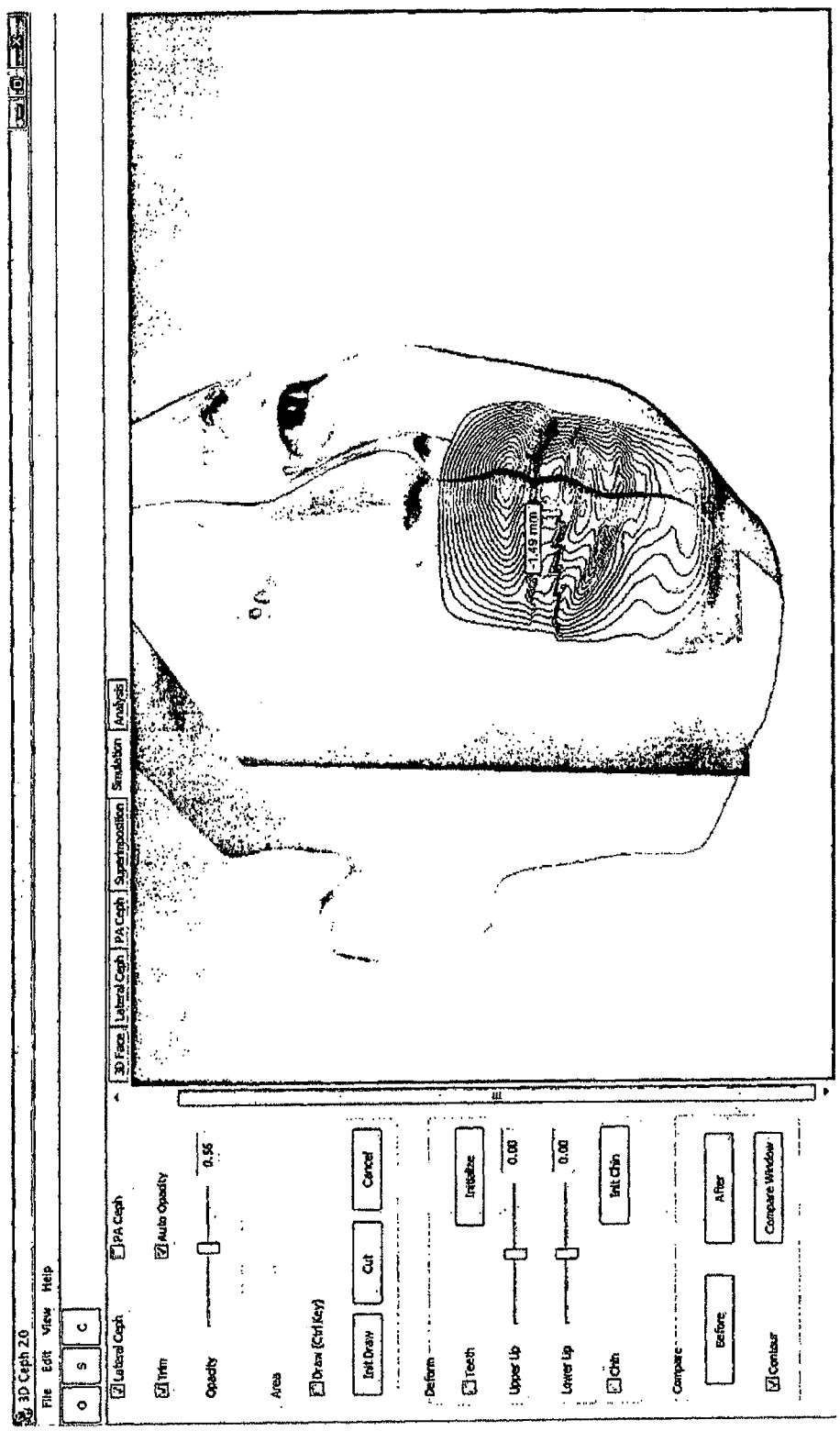
FIG. 20 is a captured image of a display window showing a predicted facial image in which the contour lines are displayed.

In other words, the user may alternately press the Before button and the After button on the right side of the screen to compare the appearances before and after the simulation. Further, the contour lines may be displayed on the predicted facial image as shown in FIG. 20.

When the Contour box on the right side of the screen is selected, the degree of transformation in the lip and jaw parts caused by the movement of the incisors may be shown in the form of the contour lines. The parts having the same degree of transformation may be connected to form a line, and such lines are respectively drawn with regard to multiple transformation amounts at regular intervals. By placing a mouse point on the contour lines, the actual amount of transformation may be displayed in millimeters. The above contour lines are displayed on the screen based on the amount of transformation of the soft skin tissues according to the skeletal change.

Meanwhile, according to the present invention, there is provided a computer-readable recording medium having stored thereon a program for providing a face adjustment image, which enables a computer to function as matching means to generate a matched image by superimposing a cephalometric image having a cranium image of a patient whose face is to be corrected with a 3D facial image of the patient, and image display means to display a predicted facial image on a screen by transforming soft skin tissues of the face according to the skeletal change in the cephalometric image. Further, there may be provided a device such as a system server or the like in which the computer-readable recording medium is stored so that the above program is delivered via networks. The recording medium may contain a program to implement the respective steps of the above-described method for providing a face adjustment image.

The preferred embodiments according to the present invention have been described as above, and it will be appreciated by a person of ordinary skill in the art that various modifications and changes can be made from the description without departing from the spirit and scope of the invention. Therefore, the above-described embodiments should be taken as illustrative and not as limiting, and thus the present invention is not limited to the above description but may be modified within the scope of the appended claims and their equivalents.

INDUSTRIAL APPLICABILITY

The present invention relates to a virtual plastic surgery simulation system and a virtual plastic surgery method used in the orthodontics and plastic surgery field, which has industrial applicability in the field of manufacturing devices and methods for the virtual plastic surgery simulation. By virtue of the method and system for providing a face adjustment image according to the invention, the change in soft skin tissues and the predicted facial image are displayed on a screen of a computer, a terminal or the like based on the skeletal change in cranium, teeth, prosthesis or the like supporting the soft skin tissues. Therefore, the change in the soft skin tissues can be predicted, thereby increasing the accuracy of a face correction operation, making it more accurate and convenient to plan the operation, and enhancing communication and medical counseling between the patient and medical staff.

What is claimed is:

1. A method for providing a face adjustment image, comprising the steps of:
    generating a matched image on a screen by superimposing a two-dimensional cephalometric image having an X-ray image for a cranium of a patient whose face is to be corrected with a three-dimensional facial image of a face of the patient acquired by photographing the face of the patient;
    receiving a change in hard tissues implemented in the two-dimensional cephalometric image;
    determining parts of soft skin tissues to be transformed by the change in the hard tissues;
    determining transformation rates of the parts of the soft skin tissues; and
    displaying on the screen a predicted facial image in which the soft skin tissues in the three-dimensional facial image are transformed based on the transformation rates in response to the change in hard tissues implemented in the two-dimensional cephalometric image in the matched image.

2. The method of claim 1, further comprising:
    determining whether operation data related to the parts of the soft skin tissues is stored in a memory unit;
    determining the transformation rates of the parts based on the operation data in response to determining that the operation data related to the parts of the soft skin tissues is stored in the memory unit; and
    determining the transformation rates of the parts based on a sine function in response to determining that the operation data related to the parts of the soft skin tissues does not exist.

3. The method of claim 1, wherein the transformation rates of the parts of the soft skin tissues are input from a user.

4. The method of claim 1, wherein the transformation rates of the parts of the soft skin tissues are determined based on a combination of operation data related to the parts of the soft skin tissues and an input from a user.

5. The method of claim 1, further comprising:
    extracting feature points of the face; and
    determining the parts of soft skin tissues to be transformed by the change in the hard tissues based on the feature points.

6. The method of claim 1, further comprising:
    adjusting transparency of a half of the three-dimensional facial image of the face of the patient in the matched image to display a half-cut matched image.

7. The method of claim 1, wherein generating the matched image comprises:
    matching a plurality of first alignment points arranged on the three-dimensional facial image to superimpose the three-dimensional facial image and the two-dimensional cephalometric image with a plurality of second alignment points arranged on the positions corresponding to those of the first alignment points on the outline of the two-dimensional cephalometric image, which is formed by the soft skin tissues, so that the three-dimensional facial image and the two-dimensional cephalometric image are superimposed.

8. The method of claim 7, further comprising displaying matching alignment lines on the screen,
    wherein the matching alignment lines are respectively formed on the first alignment points, and their orientations and lengths may be adjusted to achieve one-to-one correspondence of the first alignment points to the second alignment points.

9. The method of claim 7, wherein the matched image by superimposing the two-dimensional cephalometric image is generated on a cross section of the three-dimensional facial image divided by a matching reference line arranged on the three-dimensional facial image.

10. The method of claim 9, wherein the matching reference line is a vertical line dividing the three-dimensional facial image to the left and right sides, and the two-dimensional cephalometric image is a lateral X-ray image obtained by photographing a head of the patient on a lateral side perpendicular to a front side of the face.

11. The method of claim 1, wherein generating the matched image comprises
    adjusting a size and orientation of the two-dimensional cephalometric image to the same as those of the three-dimensional facial image.

12. The method of claim 11, wherein:
    the first alignment points comprise a pair of facial alignment points;
    the second alignment points comprise a pair of outline alignment points located on the positions corresponding to those of the facial alignment points; and
    adjusting the size and orientation of the two-dimensional cephalometric image is performed by matching the size and orientation of a first vector formed by the facial alignment points and a second vector formed by the outline alignment points.

13. The method of claim 1, wherein the transformation of the soft skin tissues results from at least one of tooth migration and cranial transformation.

14. The method of claim 1, further comprising selectively displaying contour lines for showing the change in the soft skin tissues on the predicted facial image, or simultaneously or sequentially displays the predicted facial images before and after a simulation on the screen.

15. The method of claim 1, wherein generating the matched image on the screen by superimposing the two-dimensional cephalometric image with the three-dimensional facial image comprises:
    generating a two-dimensional profile line on the three-dimensional facial image; and
    superimposing the two-dimensional cephalometric image with the three-dimensional facial image such that the two-dimensional cephalometric is placed on a two-dimensional plane encompassing the two-dimensional profile line.

16. A system for providing a face adjustment image, comprising:
    a controller programmed to:
        generate a matched image on a screen by superimposing a two-dimensional cephalometric image having an X-ray image for a cranium of a patient whose face is to be corrected with a three-dimensional facial image of a face of the patient acquired by photographing the face of the patient;
        receive a change in hard tissues implemented in the two-dimensional cephalometric image;
        determine parts of soft skin tissues to be transformed by the change in the hard tissues;
        determine transformation rates of the parts of the soft skin tissues; and
        display on the screen a predicted facial image in which the soft skin tissues in the three-dimensional facial image are transformed based on the transformation rates in response to the change in hard tissues implemented in the two-dimensional cephalometric image in the matched image.

17. The system of claim 16, wherein the controller is further programmed to:
    determine whether operation data related to the parts of the soft skin tissues is stored in a memory unit;
    determine the transformation rates of the parts based on the operation data in response to determining that the operation data related to the parts of the soft skin tissues is stored in the memory unit; and
    determine the transformation rates of the parts based on a sine function in response to determining that the operation data related to the parts of the soft skin tissues does not exist.

18. The system of claim 16, wherein the transformation rates of the parts of the soft skin tissues are input from a user.

19. The system of claim 16, wherein the transformation rates of the parts of the soft skin tissues are determined based on a combination of operation data related to the parts of the soft skin tissues and an input from a user.

20. A non-transitory computer-readable recording medium having stored thereon a program for providing a face adjustment image, when executed by a processor, causing a computer to:
    generate a matched image on a screen by superimposing a two-dimensional cephalometric image having an X-ray image for a cranium of a patient whose face is to be corrected with a three-dimensional facial image of a face of the patient acquired by photographing the face of the patient;
    receive a change in hard tissues implemented in the two-dimensional cephalometric image;
    determine parts of soft skin tissues to be transformed by the change in the hard tissues;
    determine transformation rates of the parts of the soft skin tissues; and display on the screen a predicted facial image in which the soft skin tissues in the three-dimensional facial image are transformed based on the transformation rates in response to the change in hard tissues implemented in the two-dimensional cephalometric image in the matched image.

* * * * *